(12) United States Patent
Ahmadi

(10) Patent No.: US 10,285,904 B2
(45) Date of Patent: May 14, 2019

(54) MEDICATION GUIDANCE SYSTEM AND METHOD

(71) Applicant: Ahmad H. Ahmadi, Sugar Land, TX (US)

(72) Inventor: Ahmad H. Ahmadi, Sugar Land, TX (US)

(73) Assignee: DEA HEALTH SOLUTIONS, LLC, Sugar Land, TX (US)

( * ) Notice: Subject to any disclaimer, the term of this patent is extended or adjusted under 35 U.S.C. 154(b) by 886 days.

(21) Appl. No.: 14/746,081

(22) Filed: Jun. 22, 2015

(65) Prior Publication Data
US 2016/0367435 A1 Dec. 22, 2016

(51) Int. Cl.
*A61J 1/03* (2006.01)
*G06F 19/00* (2018.01)

(52) U.S. Cl.
CPC ............ *A61J 1/035* (2013.01); *A61J 1/03* (2013.01); *G06F 19/00* (2013.01); *G06F 19/3456* (2013.01)

(58) Field of Classification Search
CPC .. G06Q 50/22; G06Q 50/24; A61J 1/00; A61J 1/03; A61J 1/035; A61J 7/04
See application file for complete search history.

(56) References Cited

U.S. PATENT DOCUMENTS

| 6,601,729 | B1 * | 8/2003 | Papp | A61J 7/0084 |
| | | | | 206/528 |
| 8,193,918 | B1 * | 6/2012 | Shavelsky | A61J 7/04 |
| | | | | 340/309.16 |
| 9,241,871 | B2 * | 1/2016 | Intini | A61J 1/16 |
| 2013/0319902 | A1 * | 12/2013 | Tufi | A61J 1/035 |
| | | | | 206/534 |

* cited by examiner

*Primary Examiner* — Elaine Gort
*Assistant Examiner* — Evangeline Barr

(57) ABSTRACT

A medication guidance system and method that is employed for inventory management and to facilitate the proper administration of medication utilizes a medication blister cassette. A blister housing for receiving a medication package is positioned within a cassette case and is electronically connected to a cassette microcomputer. The blister housing has a plurality of blister housing compartments for receiving a plurality of blisters of the medication package. The cassette microcomputer logs user activities, displays medication information, alerts a user to administer medication, and activates a compartment light for each of the plurality of blister housing compartments. The cassette microcomputer can also communicate with a user computer and a database center through a transceiver. The user can interact with the cassette microcomputer through a user interaction assembly including components from the group consisting of a display screen, a speaker, a vibrator, a microphone, a biometric sensor, or a combination thereof.

10 Claims, 33 Drawing Sheets

MEDICATION GUIDANCE SYSTEM AND METHOD

FIELD OF THE INVENTION

The present invention relates generally to medication administration. More specifically, the present invention is a medication guidance system and method that notifies a user of medication doses and logs the administration of medication.

BACKGROUND OF THE INVENTION

Advances in health care have helped to dramatically increase the lifespan of patients and their quality of life through the development of more effective treatments, medication, and medical technologies. However, one of the leading causes of medical patient readmission and patient fatalities is accidental patient or caregiver non-compliance with medication administration. Many patients often forget to take their medication, take too many doses of their medication, take their medication in an incorrect interval, or take the wrong medication. Additionally, patients do not keep a log of their medication intake. Incorrect administration of medication in the prescribed method can lead to serious medical complications, higher medical costs, and death. Most patients do not even keep a good medication intake log to help provide assistance in medical diagnosis. Even when patients use calendars, a caregiver, their own memory or other methods to help remind them to take a particular medication on time, there is no easy and automated way for them to verify if they are taking the correct medication or dosage. There is no easy way for a health care provider to track if their patients are taking their medication in the manner that they were prescribed. There is no easy and automated way for healthcare providers to immediately modify or cancel medication orders or for pharmaceutical manufactures to recall a medication after patient or caregivers have possession of the medication. Also, there is no easy or automated way for healthcare providers to alert patients who have taken a recalled pharmaceutical of the potential danger to the patients' lives.

Therefore it is the object of the present invention to provide a medication guidance system and method that facilitates the proper administration of medication. A medication blister cassette is used to store a medication package, wherein the medication blister cassette includes a cassette microcomputer that is able to directly retrieve a prescription profile from the medication package. The cassette microcomputer utilizes medication information from the prescription profile to generate a medication administration schedule that is used to notify a user of when to administer medication in the medication package. When the medication is to be administered, the cassette microcomputer displays the medication information through a user interaction assembly and activates a compartment light for a specific blister housing compartments from a plurality of blister housing compartments. The cassette microcomputer logs all activities of the user and can share the logged activities with an electronic device, such as a user computer or a database center, allowing a third party to monitor the administration of the medication.

The present invention is also useful for inventory management in hospital and other institutional settings. Multiple medication blister cassettes can be stored on shelves, such as in a cabinet, or in a mobile cart, wherein the medication blister cassettes are accessible to authorized personnel in order to control administration of the medication. Each medication blister cassette can be for a specific patient, multiple patients, a specific medication, multiple medications, etc. When medication is administered to patients by authorized personnel, the administration of the medication doses is recorded by the medication blister cassette and shared with the institution's database in order to maintain an inventory of the medication. This also prevents theft, as only authorized personnel are able to access the medication in the medication blister cassettes.

Furthermore, the present invention can be used to communicate with a designated caregiver (e.g. family member, nurse), physician, or pharmacist. This can be used to notify the caregiver, physician, or pharmacist when the user of the present invention does not acknowledge administration of a medication dose, cancels administration, or administers a dose that was cancelled by the physician or pharmacist. The present invention can also be used to request consultation or emergency consultation from the caregiver, physician, or pharmacist through the medication blister. Yet another communicable use of the present invention is the ability for the user to re-order medication by communicating with the physician or pharmacist through the medication blister cassette.

DETAIL DESCRIPTIONS OF THE INVENTION

Figure 1:
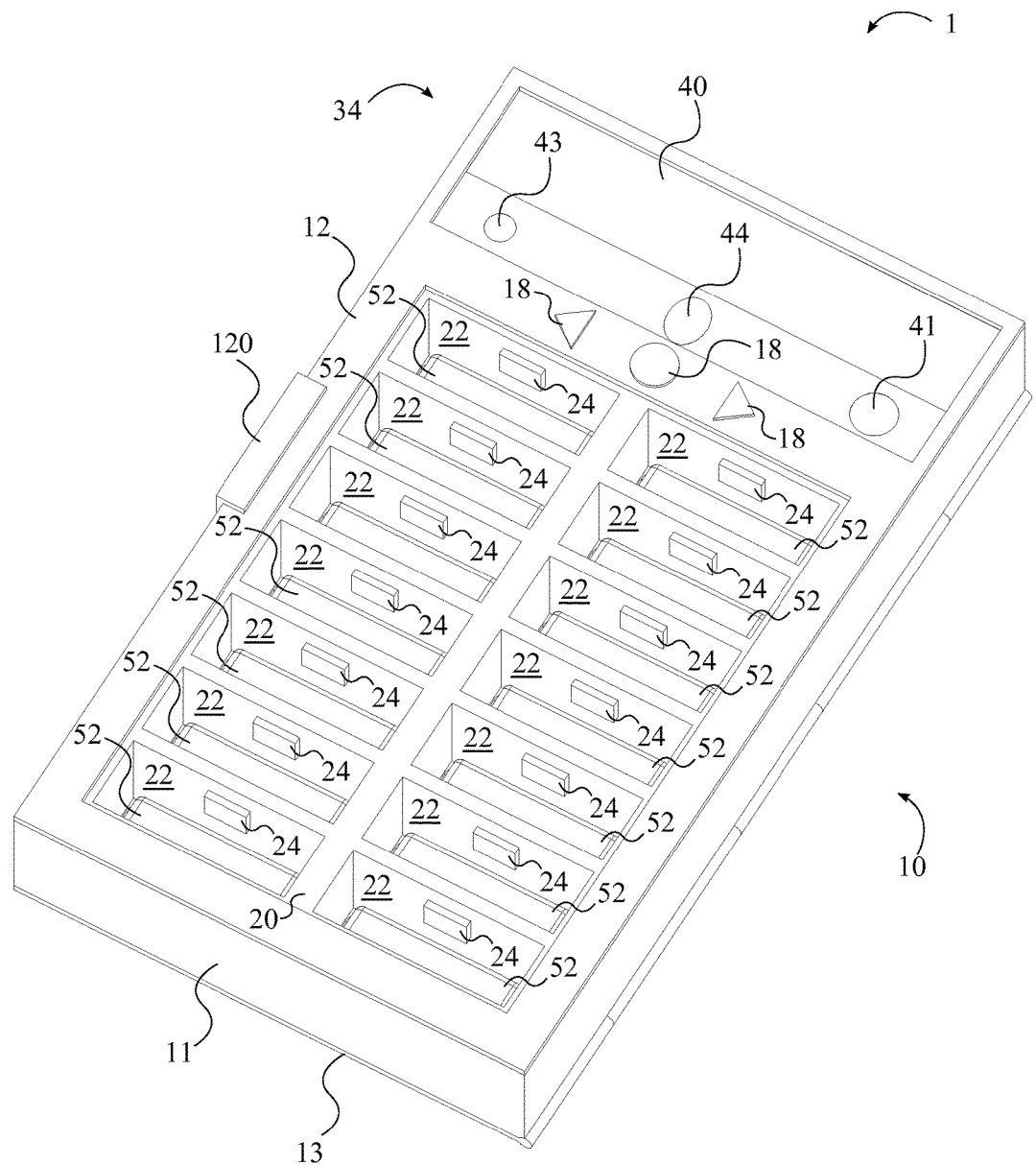
FIG. 1 is a perspective view of a medication blister cassette having a cassette case, a blister housing, a cassette microcomputer, and a medication package.

All illustrations of the drawings are for the purpose of describing selected versions of the present invention and are not intended to limit the scope of the present invention.

The present invention is a medication guidance system and method that is employed to facilitate the proper administration of medication. The system of the present invention utilizes a medication blister cassette 1, a user computer, and a database center, wherein the medication blister cassette 1 can be communicably coupled to the database center. The medication blister cassette 1 is an electronic container for holding medication and notifying a user of when to administer the medication. The method of the present invention provides a means for programming the medication blister cassette 1 with the appropriate medication profile, scheduling administration of the medication, and logging administration of the medication.

The medication blister cassette 1 comprises a cassette case 10, a blister housing 20, and a cassette microcomputer 30. The cassette case 10 provides the main containment structure for the blister housing 20 and the cassette microcomputer 30, in addition to a medication package 50. The cassette case 10 comprises a lateral cassette wall 11, a first cover 12, a second cover 13, a first cover sensor 14, a second cover sensor 15, a blister housing sensor 16, and a medication package sensor 17. In reference to FIG. 1, the first cover 12 is adjacently attached to the lateral cassette wall 11, while the second cover 13 is adjacently attached to the lateral cassette wall 11 opposite the first cover 12. In the preferred embodiment of the present invention, the first cover 12 is completely detachable from the lateral cassette wall 11, while the second cover 13 is hingedly connected to the lateral cassette wall 11 along one edge, wherein the second cover 13 can be pivoted to attach or detach from the lateral cassette wall 11.

Figure 6:
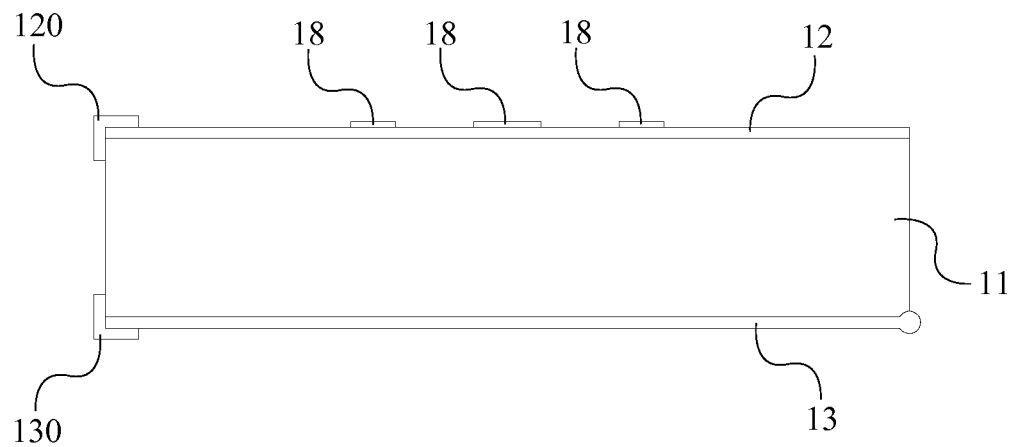
FIG. 6 is a front elevational view of the medication blister cassette.

The blister housing 20 is positioned into the cassette case 10 by detaching the first cover 12 from the lateral cassette wall 11. In reference to FIG. 7, the first cover 12 comprises a first lock 120, a medication opening 121, and a microcomputer opening 122. The first lock 120 is utilized to prevent unauthorized access into the cassette case 10 through the first cover 12. As such, the first lock 120 is positioned on the first cover 12 such that the first lock 120 engages the lateral cassette wall 11, as depicted in FIG. 6. When the first cover 12 is attached to the lateral cassette wall 11, the first lock 120 secures the first cover 12 in place, ensuring that first cover 12 cannot be detached without proper authorization. The first cover sensor 14, as shown in FIG. 8, is positioned adjacent to the front cover and is used to determine whether the first cover 12 is open or closed.

Figure 7:
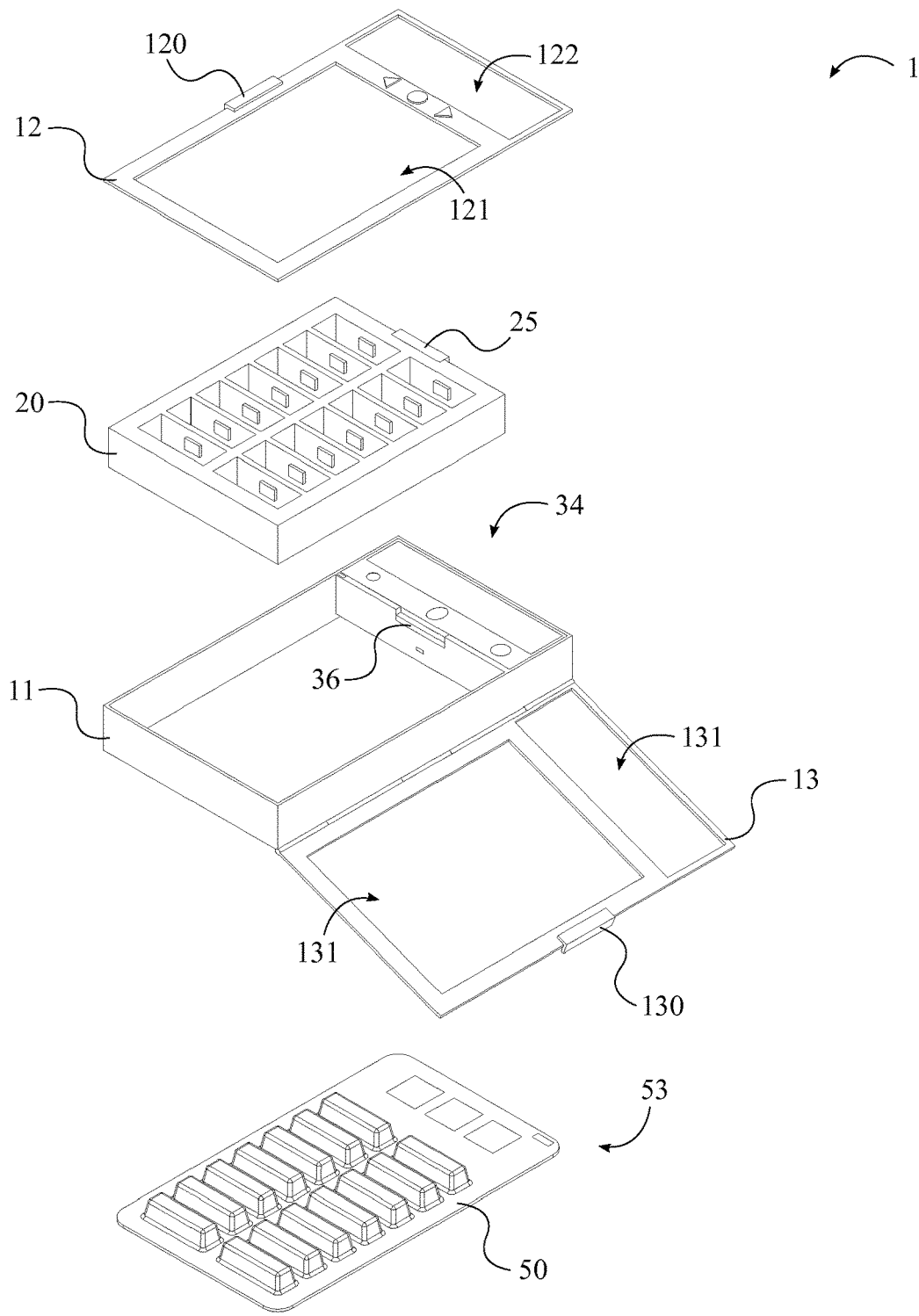
FIG. 7 is an exploded view of the medication blister cassette.
Figure 8:
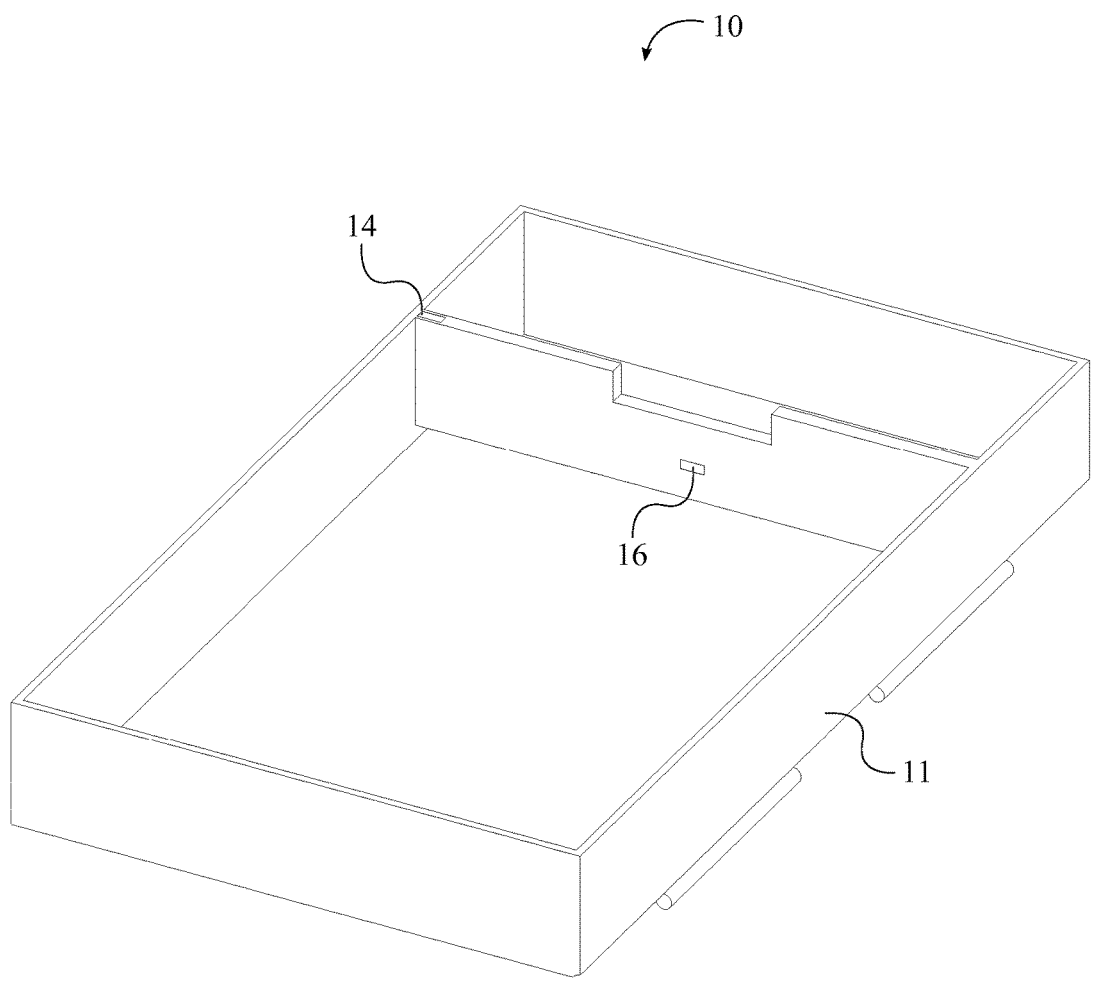
FIG. 8 is a perspective view of the cassette case, wherein a first cover sensor is positioned adjacent to a first cover when the first cover is closed and a blister housing sensor is positioned adjacent to the blister housing when the blister housing is positioned within the cassette case.

In reference to FIG. 1 and FIG. 7, the medication opening 121 traverses through the first cover 12 and is positioned adjacent to the blister housing 20 when the first cover 12 is attached to the cassette case 10. The medication opening 121 provides a viewing window through which the user can inspect the medication within the medication package 50. It is also possible for a clear piece of material, such as glass or plastic, to be fixed within the medication opening 121, such that the blister housing 20 cannot be physically accessed through the medication opening 121. Similar to the medication opening 121, the microcomputer opening 122 traverses through the first cover 12 and provides a viewing window through which the user can access and interact with the cassette microcomputer 30. As such, the microcomputer opening 122 is positioned adjacent to the cassette microcomputer 30 when the first cover 12 is attached to the cassette case 10.

The medication package 50 is positioned into the cassette case 10 by detaching the second cover 13 from the lateral cassette wall 11. In reference to FIG. 7, similar to the first cover 12, the second cover 13 comprises a second lock 130 and an at least one medication package opening 131. The second lock 130 is utilized to prevent unauthorized access into the cassette case 10 through the second cover 13. As such, the second lock 130 is positioned on the second cover 13 such that the second lock 130 engages the lateral cassette wall 11, as depicted in FIG. 6. When the second cover 13 is attached to the lateral cassette wall 11, the second lock 130 secures the second cover 13 in place, ensuring that second cover 13 cannot be detached without proper authorization. The second cover sensor 15 is positioned adjacent to the second cover 13 and is used to determine whether the second cover 13 is open or closed.

Figure 5:
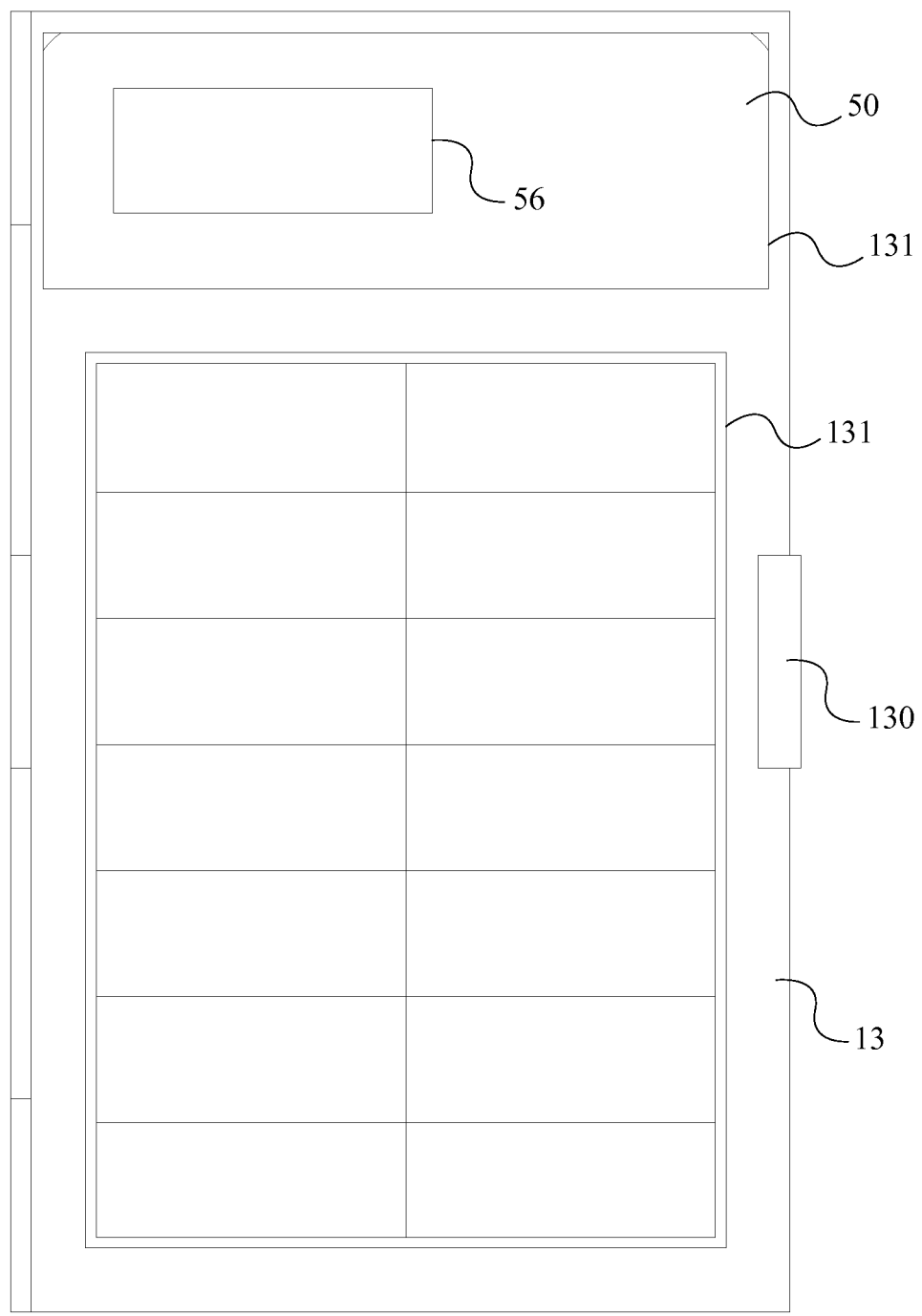
FIG. 5 is a bottom plan view of medication blister cassette.

In reference to FIG. 5 and FIG. 7, the at least one medication package opening 131 traverses through the second cover 13 and is positioned adjacent to the medication package 50 when the second cover 13 is closed. The at least one medication package opening 131 provides a viewing window through which the user can inspect the back of the medication package 50. The user can view any information displayed on the back of the medication package 50 through the at least one medication package opening 131 without having to open the second cover 13. Additionally, the at least one medication package 50 allows the user to administer the medication without having to remove the medication package 50 from the blister housing 20 and the cassette case 10.

Figure 10:
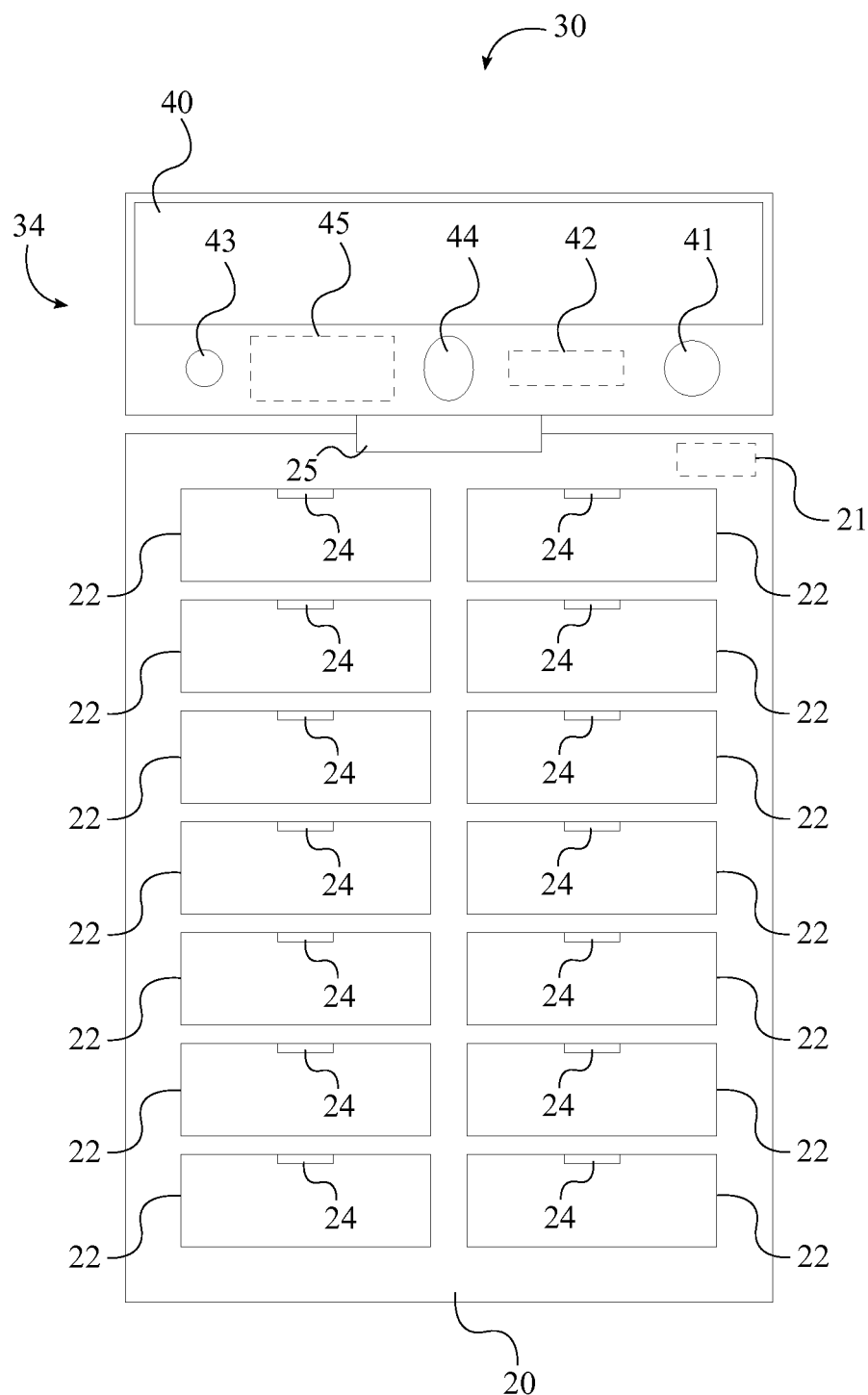
FIG. 10 is a top plan view of the blister housing connected to the cassette microcomputer, depicting an identification memory chip positioned within the blister housing, and a power source and a vibrator positioned within the cassette microcomputer.

The blister housing 20 is positioned within the cassette case 10 and, in reference to FIG. 10, comprises an identification memory chip 21, a plurality of blister housing compartments 22, a compartment light 24 for each of the plurality of blister housing compartments 22, and a first connector array 25. The blister housing sensor 16 detects whether or not the blister housing 20 is positioned within the cassette case 10. As such, the blister housing sensor 16 is positioned within the lateral cassette wall 11, adjacent to the blister housing 20. The plurality of blister housing compartments 22 dictates the medication package 50 that can be inserted into the cassette case 10, as the plurality of blister housing compartments 22 corresponds to a plurality of blisters 51 of the medication package 50. The compartment light 24 of each of the plurality of blister housing compartments 22 is utilized to indicate from which of the plurality of blisters 51 the medication should be administered. The compartment light 24 illuminates only a single blister housing from the plurality of blister housings 22 (i.e. light does not leak through the blister housing 20 into adjacent blister housings), such that the user can easily identify the blister housing from which to administer the medication and does not mistake an adjacent blister housing as the illuminated blister housing. Preferably the compartment light 24 for each of the plurality of blister housing compartments 22 is a light emitting diode (LED), however, any other type of light may be used.

Figure 11:
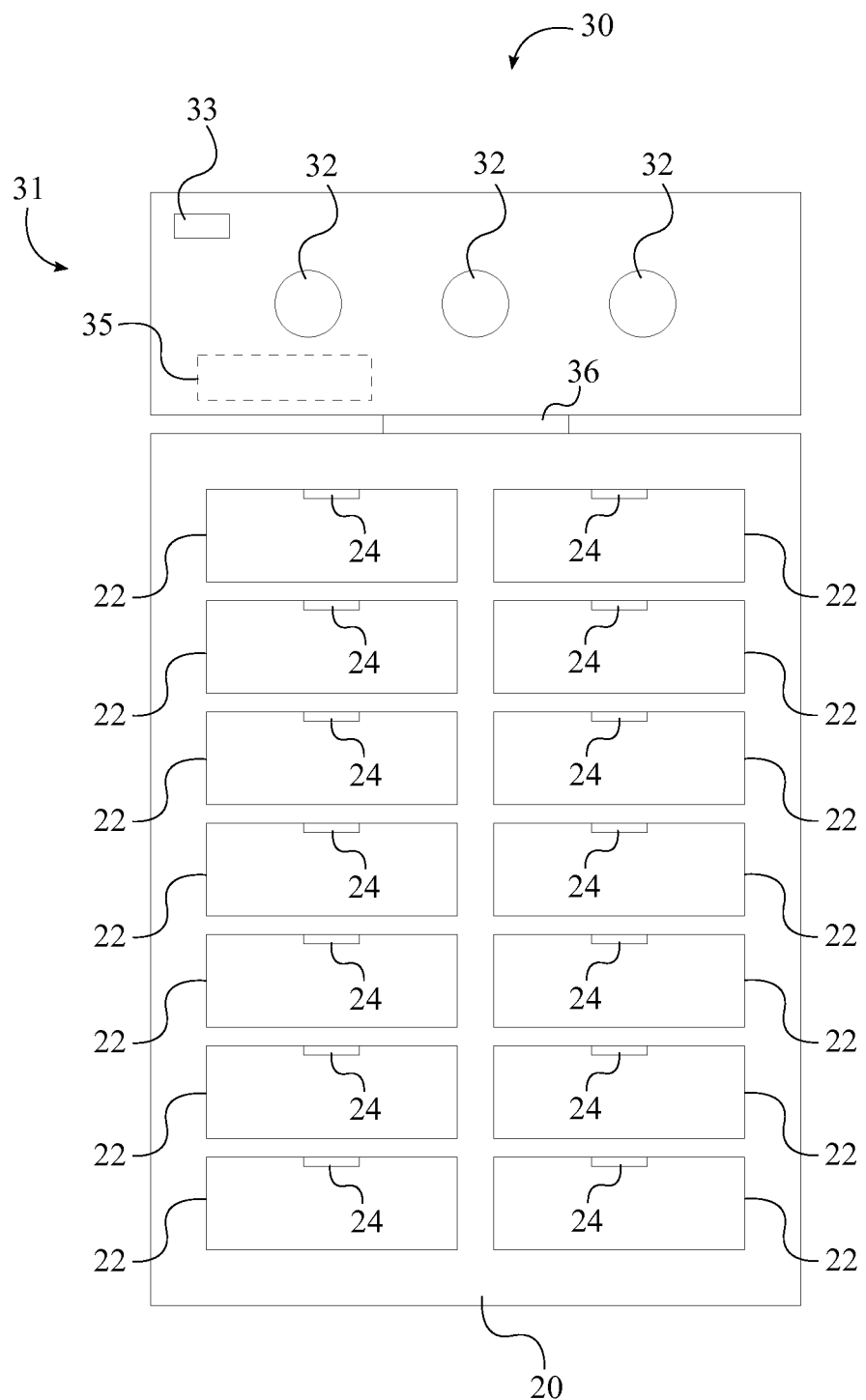
FIG. 11 is a bottom plan view of the blister housing connected to the cassette microcomputer, depicting a transceiver positioned within the cassette microcomputer.
Figure 18:
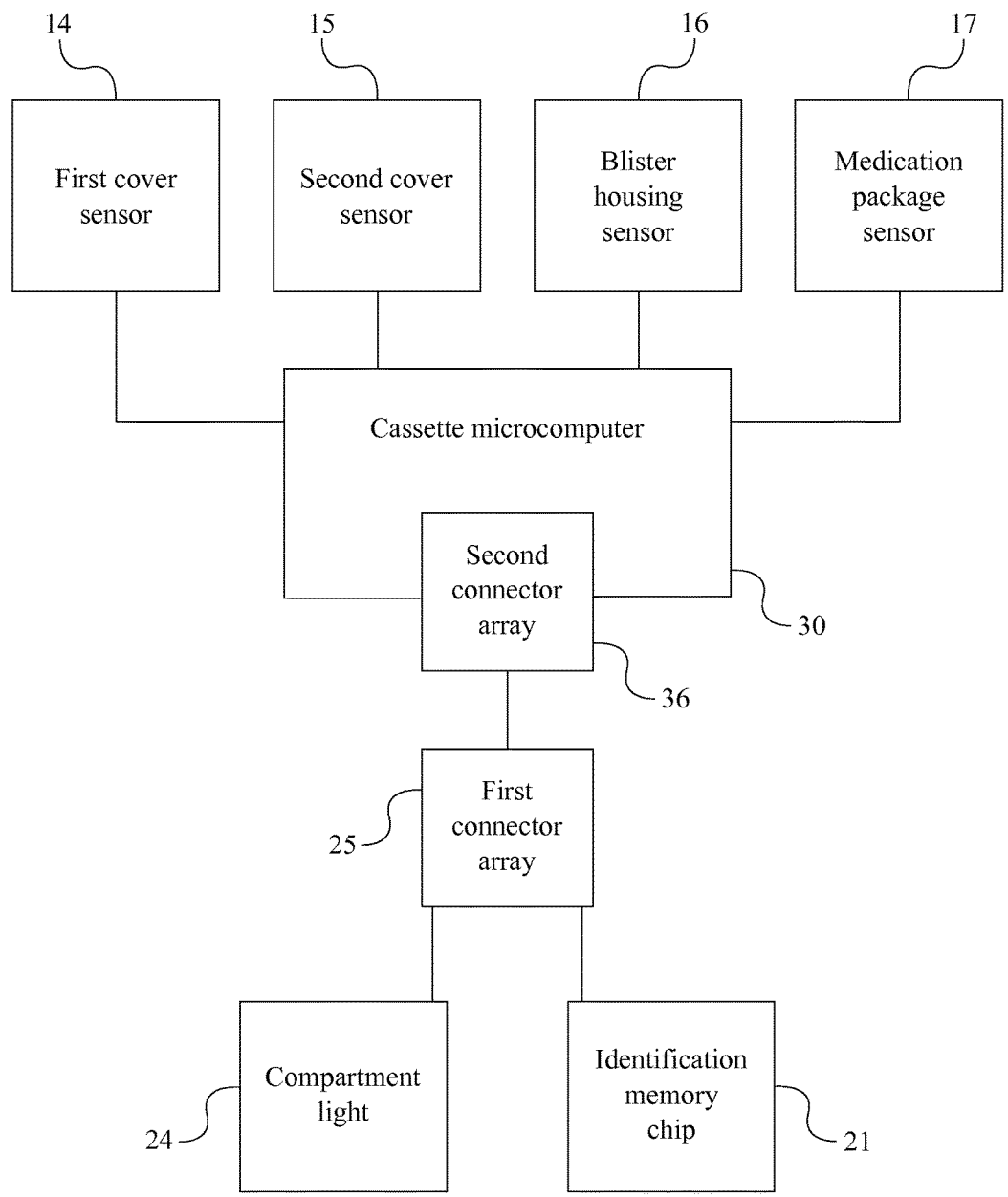
FIG. 18 is a diagram depicting the electronic connections between the cassette microcomputer and other components of the medication blister cassette.

The cassette microcomputer 30 provides the computing functionality of the medication blister cassette 1 and, in reference to FIG. 10-11, comprises a medication package reader 31, a user interaction assembly 34, a transceiver 35, and a second connector array 36. The cassette microcomputer 30 has the ability to process and execute commands, store data, and communicate with and powers components of the cassette case 10 and the blister housing 20. More specifically, the cassette microcomputer 30 communicates with and powers the first cover sensor 14, the second cover sensor 15, the blister housing sensor 16, the medication package sensor 17, the identification memory chip 21, and the compartment light 24 for each of the plurality of blister housing compartments 22. As such, the first cover sensor 14, the second cover sensor 15, the blister housing sensor 16, the medication package sensor 17, the identification memory chip 21, and the compartment light 24 for each of the plurality of blister housing compartments 22 are electronically connected to the cassette microcomputer 30, as depicted in FIG. 18.

The first lock 120 and the second lock 130 may also be electronically connected to the cassette microcomputer 30 depending on the specific locking mechanism used. If the first lock 120 and the second lock 130 utilize electronic locking mechanisms, then the first lock 120 and the second lock 130 can be electronically connected to the cassette microcomputer 30. In this way, the user can enter commands through the user interaction assembly 34 in order to lock and unlock the first lock 120 and the second lock 130. Even if the locking mechanism for the first lock 120 and the second lock 130 is mechanical, the first lock 120 and the second lock 130 can still be electronically connected to the cassette microcomputer 30, such that the cassette microcomputer 30 can monitor whether the first lock 120 and the second lock 130 are locked or unlocked.

The transceiver 35 allows the cassette microcomputer 30 to wirelessly communicate with an electronic device, such as the user computer or the database center. The user computer can be used in tandem with the medication blister cassette 1 to schedule and administer the medication, while the database center can be used to provide medication information or patient information. The user computer can be any type of computing device, such as a smartphone, desktop, or workstation terminal. The database center can be a single computing device or a network of computing devices, such as a network of servers. In other embodiments of the present invention, the medication blister cassette 1 may be able to connect to the user computer or the database center across a network through a wired connection.

The cassette microcomputer 30 includes components necessary for processing and executing commands, such as a central processing unit, application-specific integrated circuit, digital signal processor, etc. Components for storing data on the cassette microcomputer 30 may include, but are not limited to, random-access memory or hard disk drives. The cassette microcomputer 30 further includes a power source 45, as depicted in FIG. 10, for supplying current to the other components of the cassette microcomputer 30. Preferably the power source 45 is a battery, either rechargeable or non-rechargeable. If a rechargeable battery is used, then a charging port may be provided through the cassette case 10, such that the power source 45 does not need to be removed. In addition to providing current to the other components of the cassette microcomputer 30, the power source 45 supplies current to the first cover sensor 14, the second cover sensor 15, the blister housing sensor 16, the medication package sensor 17, the identification memory chip 21, and the compartment light 24 for each of the plurality of blister housing compartments 22.

Figure 12:
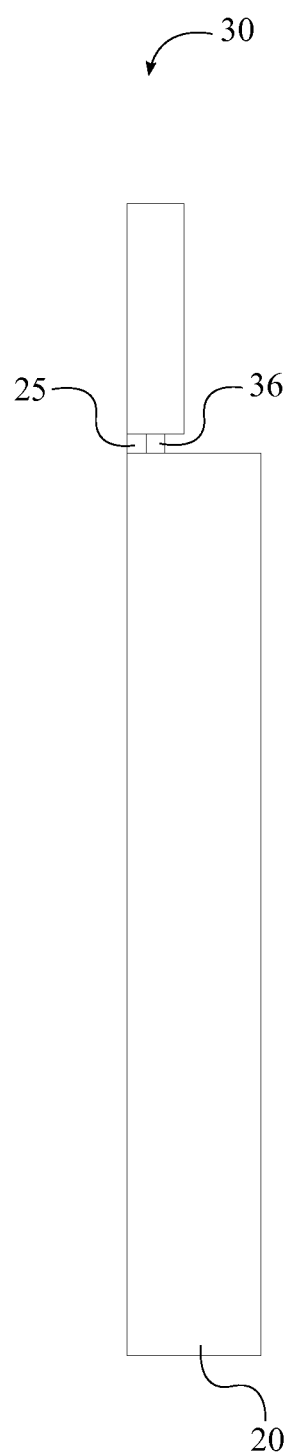
FIG. 12 is a right-side elevational view of the blister housing connected to the cassette microcomputer through a first connector array and a second connector array.

In reference to FIG. 12 and FIG. 18, the identification memory chip 21 and the compartment light 24 for each of the plurality of blister housing compartments 22 are electronically connected to the cassette microcomputer 30 through the first connector array 25 and the second connector array 36. As such, the identification memory chip 21 and the compartment light 24 for each of the plurality of blister housing compartments 22 are electronically connected to the first connector array 25. When the blister housing 20 is positioned into the cassette case 10, the first connector array 25 engages the second connector array 36, wherein the first connector array 25 is attached and electronically connected to the second connector array 36.

When the first connector array 25 engages the second connector array 36, the cassette microcomputer 30 communicably connects to the identification memory chip 21. The identification memory chip 21 is programmed with blister housing 20 information to identify the specific number of the plurality of blister housing compartments 22, and the shape and position of each of the plurality of blister housing compartments 22. The cassette microcomputer 30 reads the blister housing 20 information and stores the blister housing 20 information. The blister housing 20 information dictates to the cassette microcomputer 30 the medication package 50 that can be used with the blister housing 20. If the user attempts to insert an improper medication package 50, then the cassette microcomputer 30 can notify the user through the user interaction assembly 34.

In reference to FIG. 8, the first cover sensor 14 monitors the position of the first cover 12, and is used to determine whether the first cover 12 is open or closed. Electronic signals are sent from the first cover sensor to the cassette microcomputer 30, wherein the cassette microcomputer 30 determines the position of the first cover 12. If the first cover 12 is opened without proper authorization, then the cassette microcomputer 30 can notify the user through the user interaction assembly 34 or the transceiver 35.

Figure 9:
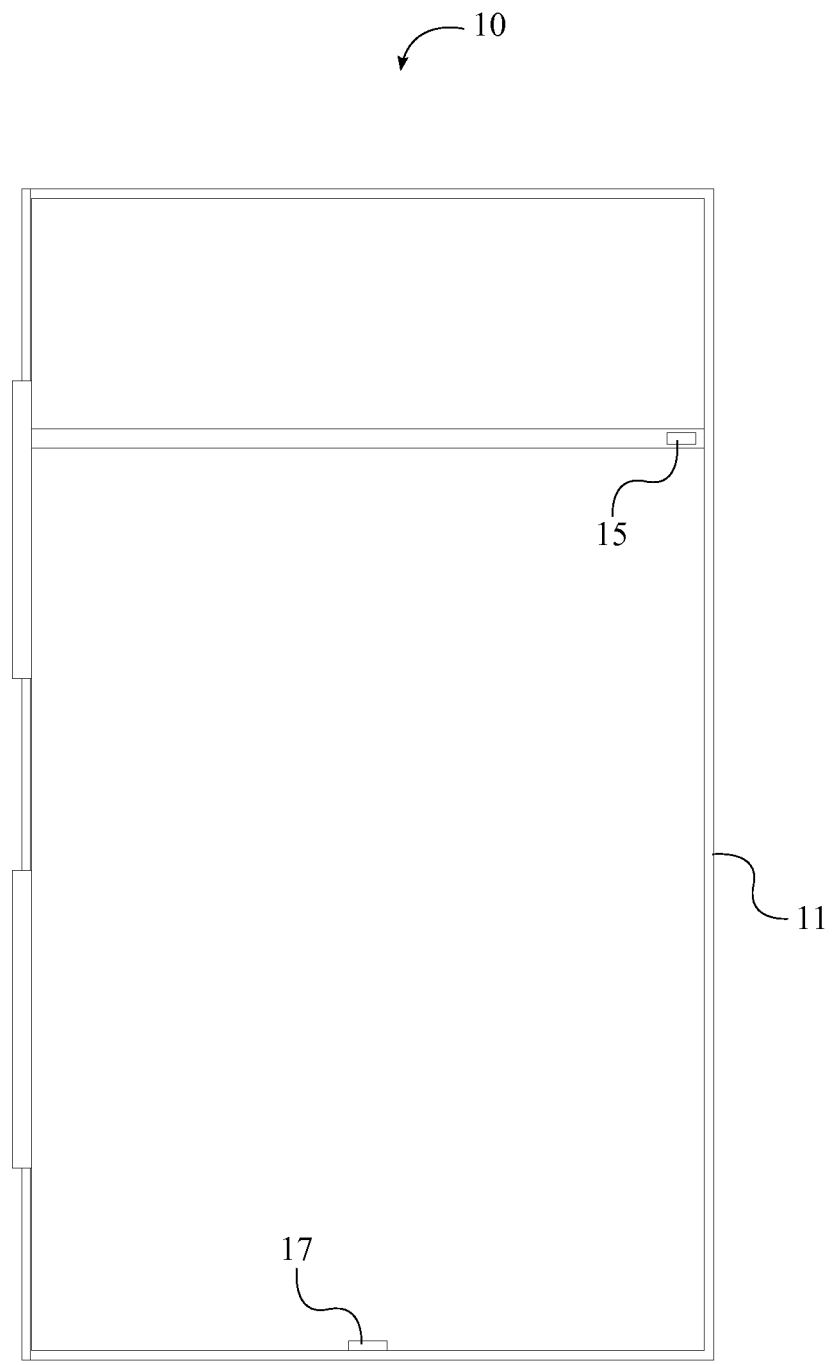
FIG. 9 is a bottom plan view of the cassette case, wherein a second cover sensor is positioned adjacent to a second cover when the second cover is closed and a medication package sensor is positioned adjacent to the medication package when the medication package is positioned within the cassette case.

In reference to FIG. 9, similar to the first cover sensor 14, the second cover sensor 15 monitors the position of the second cover 13, and is used to determine whether the second cover 13 is open or closed. Electronic signals are sent from the second cover sensor 15 to the cassette microcomputer 30, wherein the cassette microcomputer 30 determines the position of the second cover 13. If the second cover 13 is opened without proper authorization, then the cassette microcomputer 30 can notify the user through the user interaction assembly 34 or the transceiver 35.

In reference to FIG. 8, the blister housing sensor 16 detects whether or not the blister housing 20 is positioned within the cassette case 10. Electronic signals are sent from the blister housing sensor 16 to the cassette microcomputer 30, such that the cassette microcomputer 30 knows whether or not the blister housing 20 is positioned within the cassette case 10. If the cassette microcomputer 30 detects the blister housing 20 within the cassette case 10 but cannot read the identification memory chip 21, then the cassette microcomputer 30 can notify the user of a faulty connection between the first connector array 25 and the second connector array 36 through the user interaction assembly 34 or the transceiver 35.

In reference to FIG. 9, the medication package sensor 17 detects whether or not the medication package 50 is positioned within the cassette case 10. Electronic signals are sent from the medication package sensor 17 to the cassette microcomputer 30, such that the cassette microcomputer 30 knows whether or not the medication package 50 is positioned within the cassette case 10. If the medication package 50 is removed before all of the medication has been administered, then the cassette microcomputer 30 can log the action or notify the user through the user interaction assembly 34 or the transceiver 35.

The user interaction assembly 34 provides a number of different means for interaction between the user and the cassette microcomputer 30, and is accessible through the first cover 12 as depicted in FIG. 1. In reference to FIG. 10, in the preferred embodiment of the present invention, the user interaction assembly 34 comprises a display screen 40, a speaker 41, a vibrator 42, a microphone 43, and a biometric sensor 44. The display screen 40 is visible through the first cover 12 and is used to visually provide the medication information to the user. Additionally, the display screen 40 can be used to display notifications, such as when the medication should be administered. Preferably the display screen 40 utilizes a liquid crystal display or LED display, however, any other type of display may be used. The speaker 41 and the vibrator 42 are also used to alert the user of notifications; the display screen 40, the speaker 41, and the vibrator 42 can be used separately or in combination with each other. The speaker 41 can also be used to verbally dictate the medication information to the user.

The microphone 43 is used to record information dictated by the user, or to execute verbal commands dictated by the user. The cassette microcomputer 30 can be programmed to recognize verbal commands for executing specific functions, such as retrieving the medication information or a prescription profile. The display screen 40 can also optionally be a touchscreen, wherein the user can interact with the cassette microcomputer 30 through the display screen 40. If the display screen 40 is not a touchscreen, then additional control buttons 18 may be provided through the cassette case 10 to allow the user to interact with the cassette microcomputer 30. Through the display screen 40 or the additional control buttons 18, the user can initiate commands to execute the specific functions of the cassette microcomputer 30.

The biometric sensor 44 is used to authenticate the user. The biometric sensor 44 may be used to authenticate access to the specific functions of the cassette microcomputer 30, the medication information, the prescription profile, etc. Additionally, the biometric sensor 44 can be used to authenticate unlocking the first lock 120 and the second lock 130, if the first lock 120 and the second lock 130 employ an electronic locking mechanism. The microphone 43 can also be used to identify and authenticate the user through verbal inputs and voice recognition, while the touchscreen or the additional control buttons 18 can be used to enter a code to authenticate the user. Authentication can be provided separately through the biometric sensor 44, the microphone 43, the display screen 40, the additional control buttons 18, or through a combination thereof.

The medication package reader 31 is used to identify the medication package 50. In the preferred embodiment of the present invention, the medication package reader 31 is positioned opposite the user interaction assembly 34 about the cassette microcomputer 30; the medication package reader 31 being accessible through the second cover 13. Furthermore, in the preferred embodiment of the present invention, the medication package reader 31 comprises an at least one camera 32 and a radio-frequency identification (RFID) reader 33 as depicted in FIG. 11. The medication package reader 31 is used to collect information from a medication package identifier 53, depicted in FIG. 13. The medication package identifier 53 is an at least one scannable code 54, an RFID tag 55, or a combination of both. The at least one scannable code 54 can be a barcode, quick response code, or any other type of code able to retain or relate to coded data.

The medication package identifier 53 either contains information for the prescription profile or a reference to where the prescription profile is stored in the central database. The prescription profile contains a plethora of information in regards to the user and the medication; such information may include, but is not limited to, the brand name or the generic name of the medication, the number of doses, the lot number, the expiration date, scheduling for the medication, prescription number, medication administration information, patient name, patient address, patient phone number, doctor name, doctor address, doctor phone number, pharmacy name, pharmacy address, and pharmacy phone number.

Figure 13:
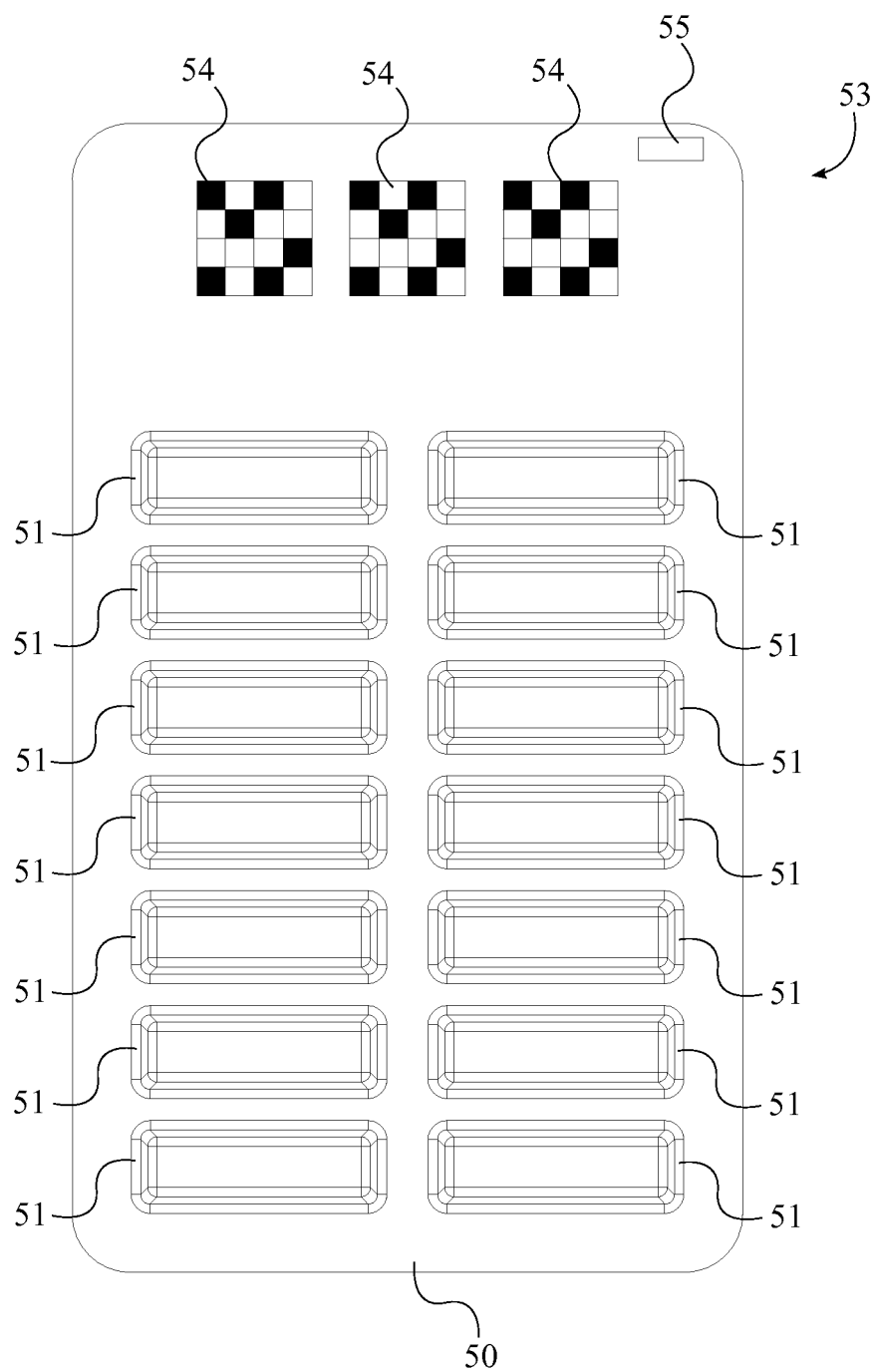
FIG. 13 is a top plan view of the medication package, depicting a medication package identifier that is positioned adjacent to a medication package reader of the cassette microcomputer when the medication package is positioned within the cassette case.

In reference to FIG. 13, the medication package identifier 53 is positioned on the front of the medication package 50, adjacent to the plurality of blisters 51. The medication package identifier 53 is positioned on the medication package 50 such that when the medication package 50 is positioned into the cassette case 10, the medication package identifier 53 is positioned adjacent to the medication package reader 31; the RFID tag 55 being positioned adjacent to the RFID reader 33, and the at least one scannable code 54 being positioned adjacent to the at least one camera 32. This allows the medication package reader 31 to scan the medication package identifier 53 in order to allow the cassette microcomputer 30 to retrieve the prescription profile.

Figure 14:
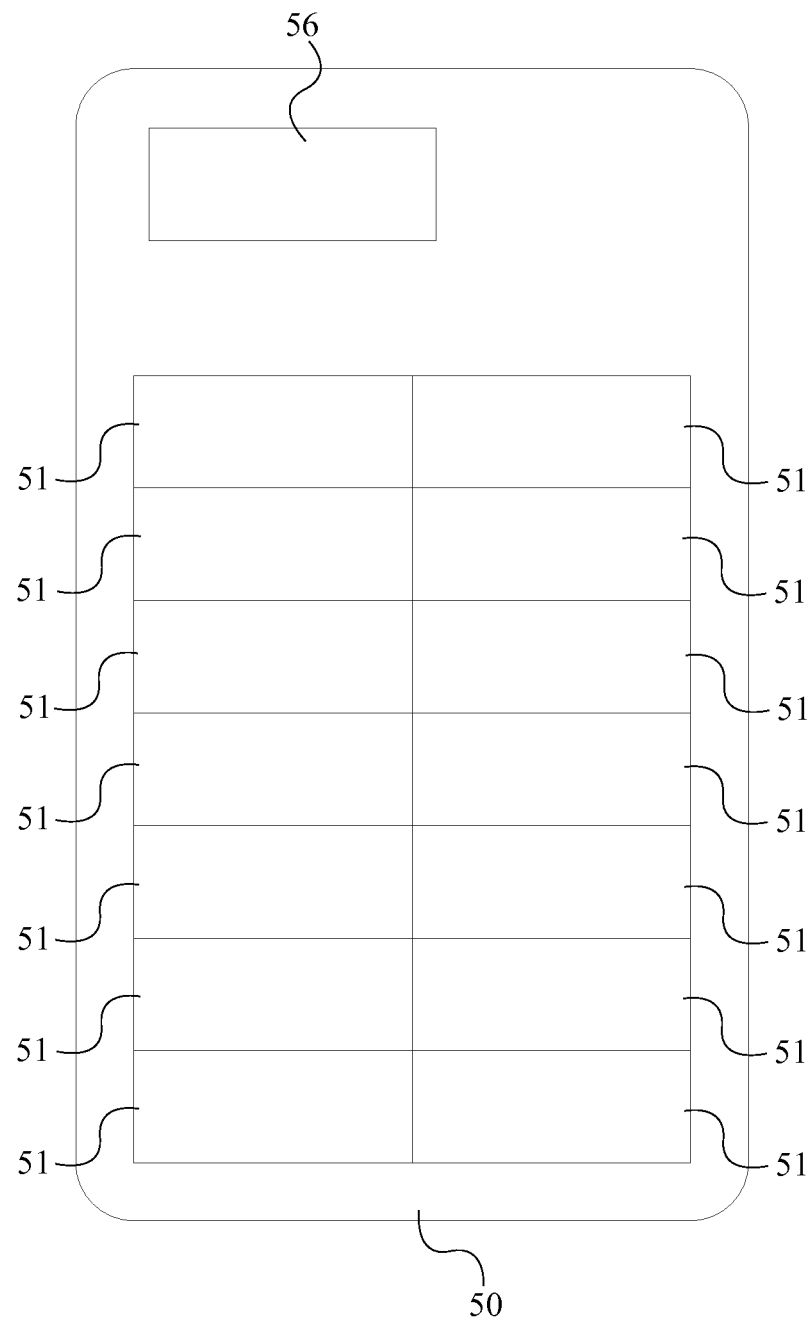
FIG. 14 is a bottom plan view of the medication package.

In reference to FIG. 14, the medication package 50 further comprises a prescription labeling 56 that is positioned on the medication package 50 opposite the medication package identifier 53. In this way, the prescription labeling 56 is positioned adjacent to the second cover 13, wherein the prescription labeling 56 is visible through the at least one medication package opening 131 of the second cover 13 as depicted in FIG. 5. The prescription labeling 56 includes a summary of information prescription profile, such that said summary of information is readily accessible to the user without having to utilize the cassette microcomputer 30.

Figure 15:
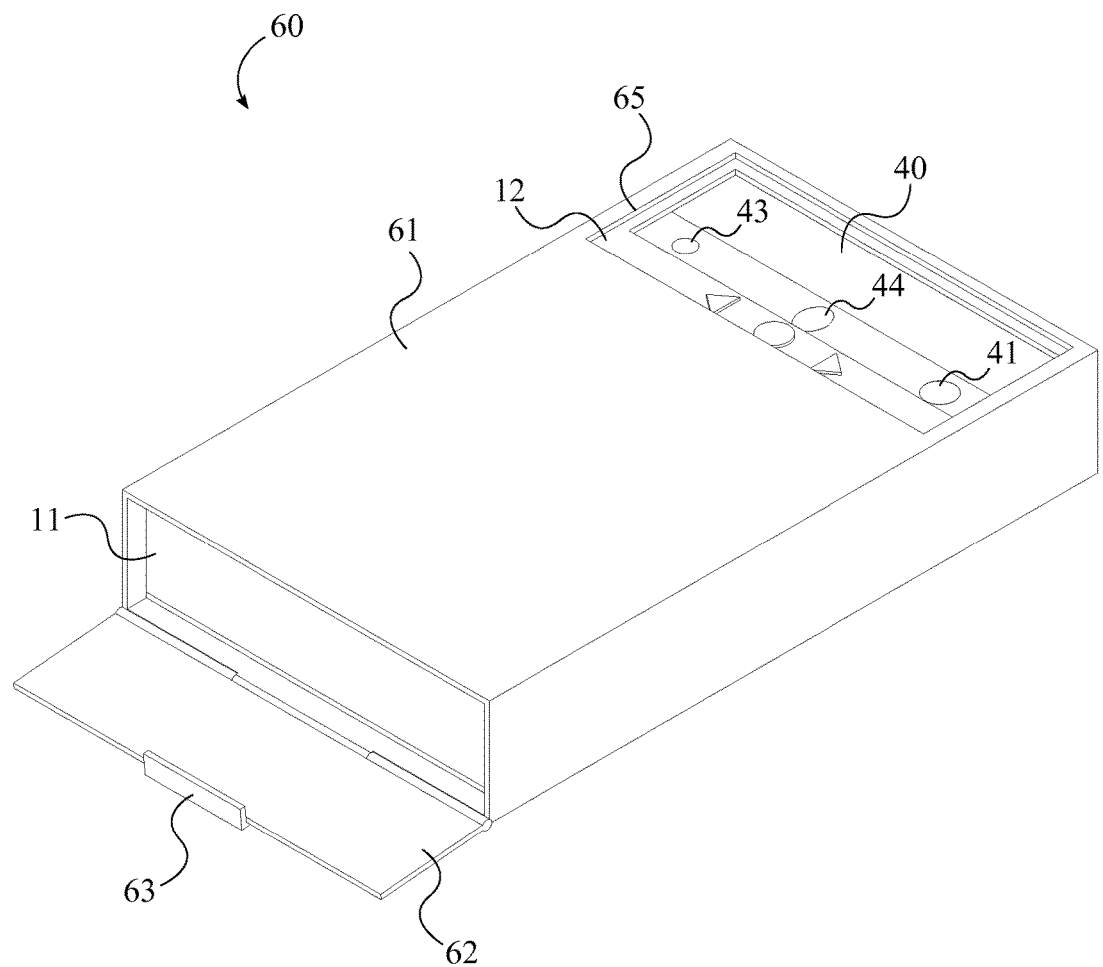
FIG. 15 is a perspective view of the cassette case being positioned within a protective shield, wherein an access door of the protective shield is open.
Figure 16:
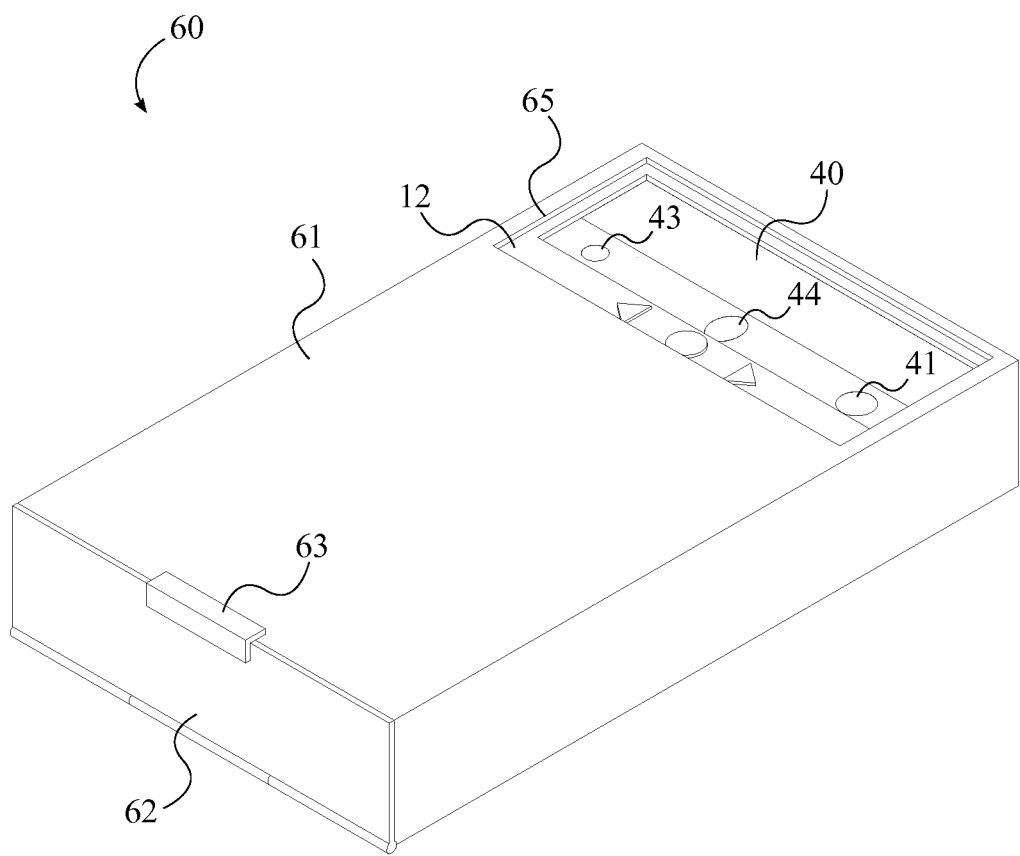
FIG. 16 is a perspective view of the cassette case positioned within the perspective shield, wherein the access door is closed.
Figure 17:
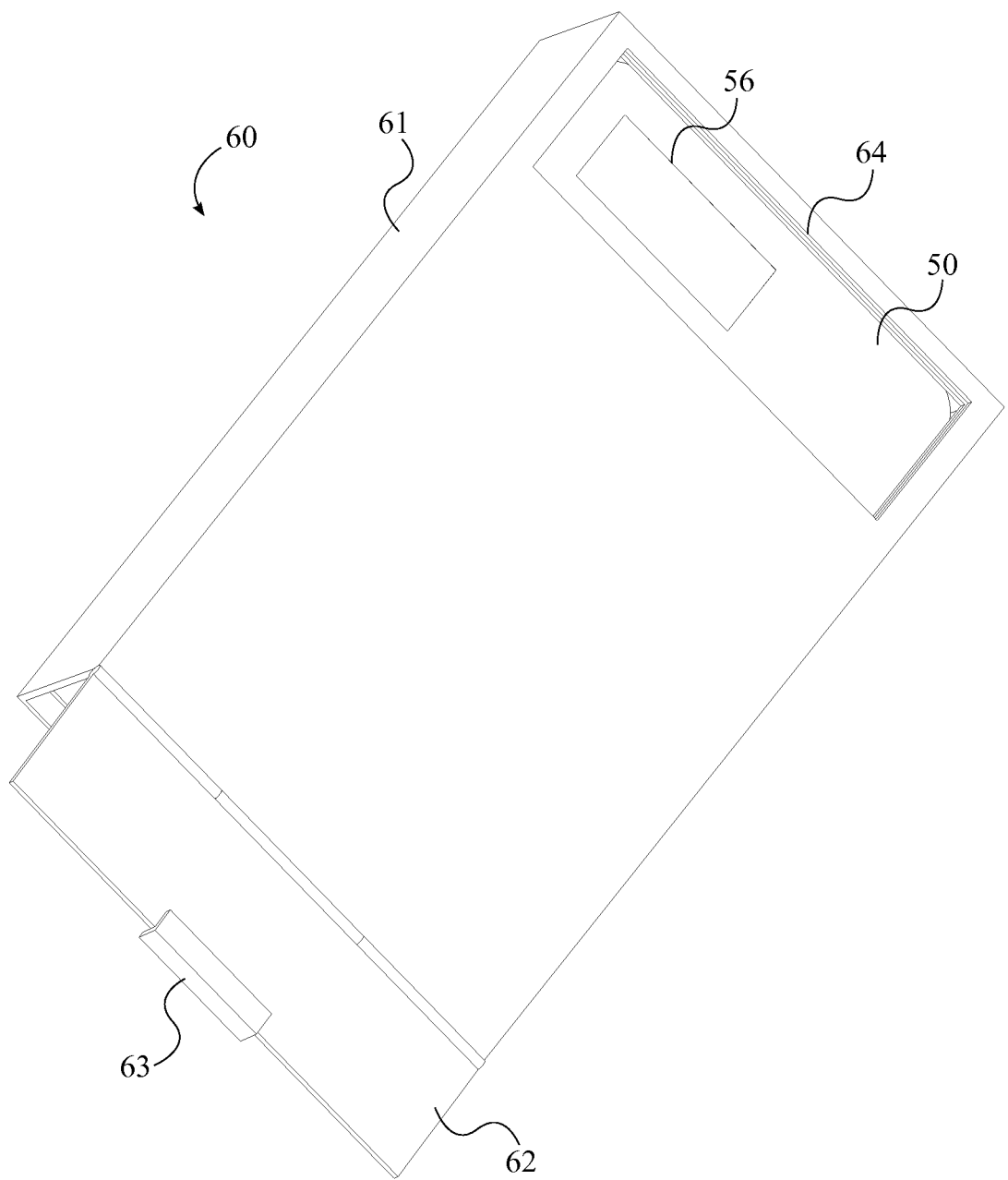
FIG. 17 is a rear perspective view of the cassette case in the protective shield, wherein a prescription labeling on the medication package is visible through a label opening of the protective shield.

In reference to FIG. 15-17, the medication blister cassette 1 may further comprise a protective shield 60. The protective shield 60 is to prevent unwarranted access to the cassette case 10, wherein the cassette case 10 is positioned within the protective shield 60. The protective shield 60 comprises a protective sleeve 61, an access door 62, a third lock 63, and a label opening 64. The access door 62 is detachably attached to the protective sleeve 61, such that the cassette case 10 can be inserted into and removed from the protective sleeve 61. Preferably the access door 62 is hingedly connected to the protective sleeve 61 along one edge, however, the access door 62 may be removably attached to the protective sleeve 61 in any other way. The label opening 64 is positioned through the protective sleeve 61 and is positioned such that the label opening 64 is adjacent to the prescription labeling 56 when the cassette case 10 is inserted into the protective sleeve 61, thus allowing the user to still read the prescription labeling 56.

In further reference to FIG. 15-16, the third lock 63 is adjacently connected to the protective sleeve 61 or the access door 62, wherein the third lock 63 then engages the access door 62 or the protective sleeve 61 respectively. The third lock 63 prevents unauthorized access to the medication within the cassette case 10 when the cassette case 10 is positioned within the protective shield 60. The third lock 63 can employ either a mechanical locking mechanism or an electronic locking mechanism. If the third lock 63 utilizes an electronic locking mechanism, then the third lock 63 may be electronically connected to the cassette microcomputer 30 or electronically connected to a second transceiver that is communicably coupled to the transceiver 35. In this way, the microphone 43, the biometric sensor 44, or the display screen 40 may be used to unlock the third lock 63, wherein the microphone 43, the biometric sensor 44, and the display screen 40 are accessible through a second opening 65 in the protective sleeve 61. Additionally, a second RFID reader may be utilized to control the third lock 63.

The method of the present invention is for the administration of medication using the medication blister cassette 1. The method for the administration of medication includes processes for placing the medication package 50 within the cassette case 10, inspecting the medication package 50, scheduling administration of the medication, administering the medication, and removing the medication package 50 from the cassette case 10. Throughout many of the processes of the method for the administration of medication, the medication blister cassette 1 is used either standalone or in combination with the user computer or the database center through an internet connection. The user described in the method of the present invention can be either a patient or a caregiver of the patient.

Figure 2:
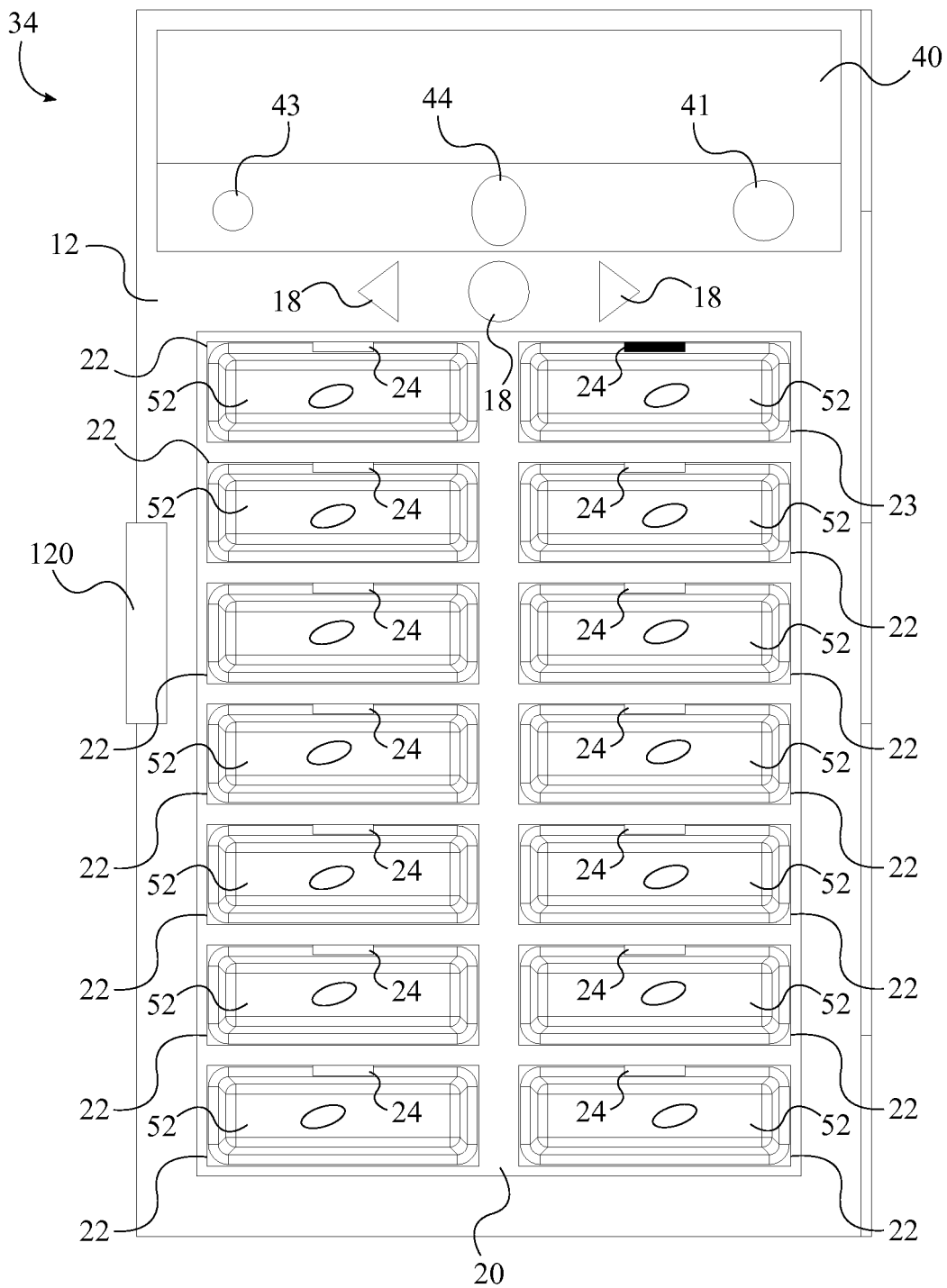
FIG. 2 is a top plan view of the medication blister cassette, wherein a plurality of blister housing compartments contain a single type of medication in a corresponding blister, and wherein a compartment light for a specific blister housing compartment is illuminated.
Figure 3:
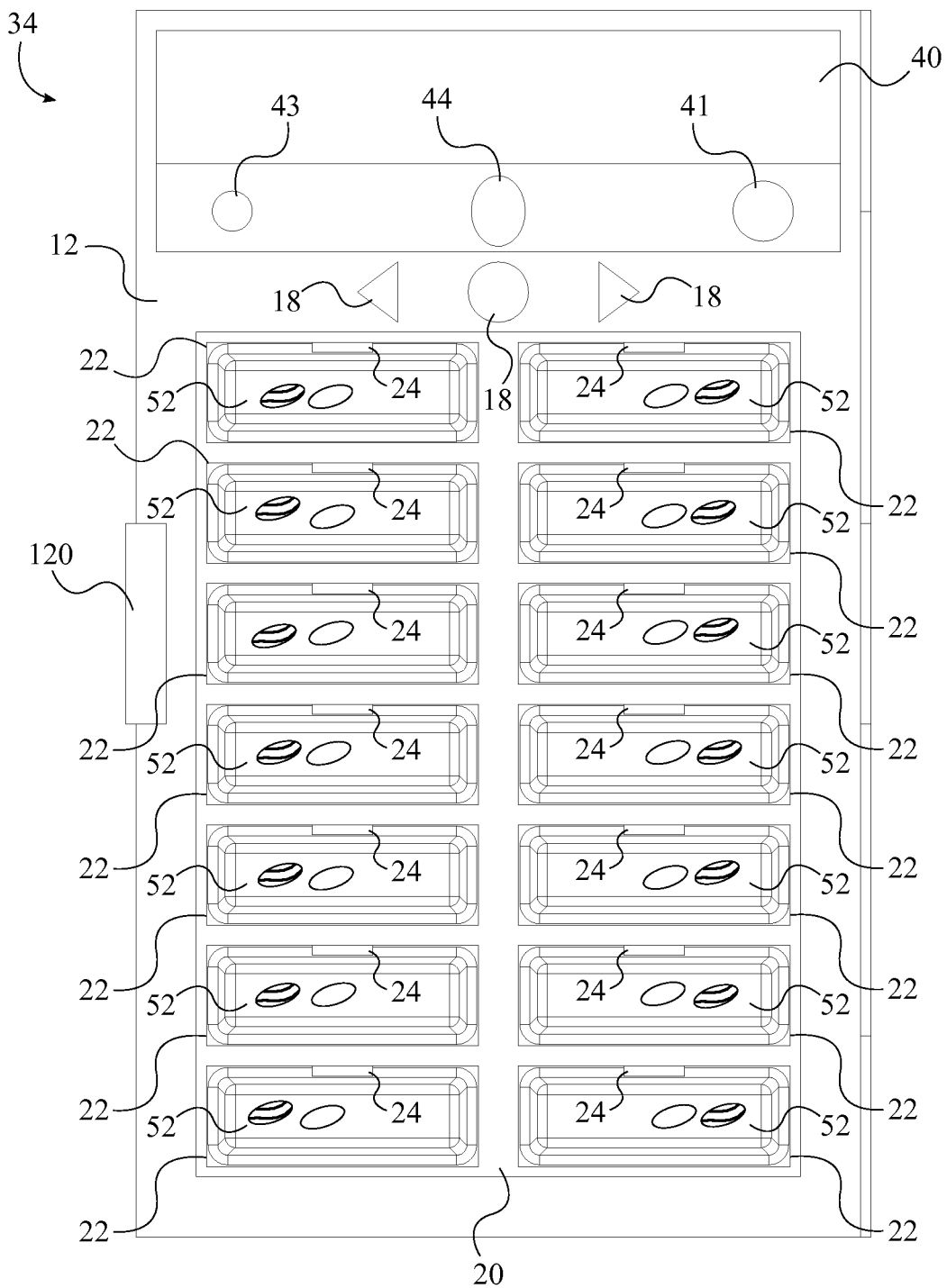
FIG. 3 is a top plan view of the medication blister cassette, wherein each of the plurality of blister housing compartments contains two types of medication.
Figure 4:
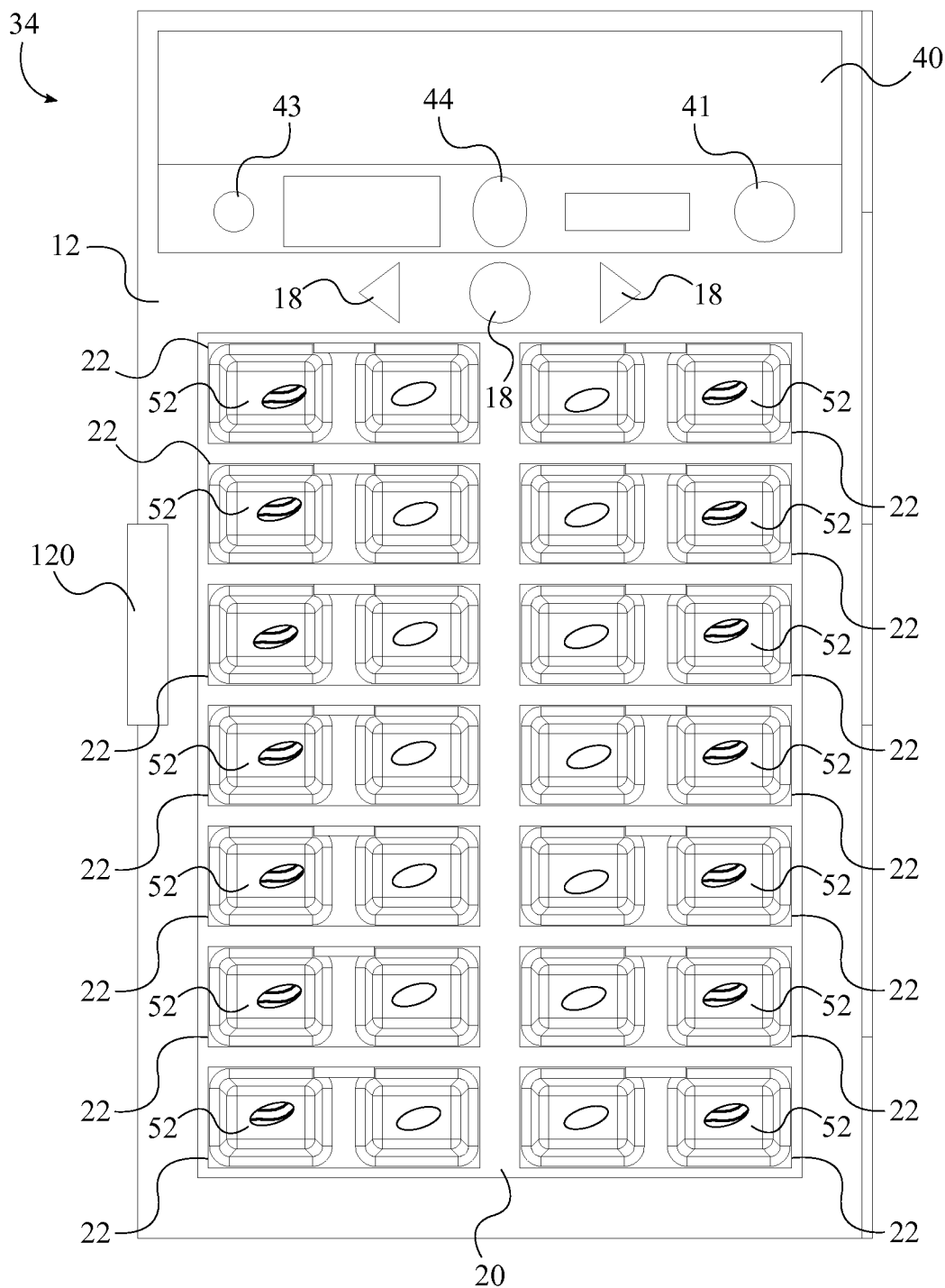
FIG. 4 is a top plan view of the medication blister cassette, wherein each of the plurality of blister housing compartments contains two types of medication separated in two corresponding blisters.

The user first selects the medication package 50 containing the medication prescribed to the patient. The user then inspects the medication package 50 and attempts to insert the medication package 50 into the blister housing 20 within the cassette case 10. When the medication package 50 is correctly positioned within the blister housing 20, a corresponding blister 52 from the plurality of blisters 51 is positioned within each of the plurality of blister housing compartments 22 as shown in FIG. 1-2. The medication in the medication package 50 may be one or multiple types of medication. If multiple types of medication are packaged, then the different types of medication may be positioned in the same blister, as shown in FIG. 3, or different blisters of the medication package 50. Even if the different types of medication are packaged in different blisters, multiple blisters may be positioned within each of the plurality of blister housing compartments 22 as shown in FIG. 4.

If the medication package 50 does not fit the blister housing 20 (i.e. the plurality of blisters 51 does not fit within the plurality of blister housing compartments 22), then the user opens the first cover 12 and removes the blister housing 20 from the cassette case 10. The user then selects the blister housing 20 that is appropriate (i.e. the plurality of blister housing compartments 22 matches the plurality of blisters 51), and positions the blister housing 20 within the cassette case 10. The user then closes the first cover 12 and, in reference to FIG. 19, the cassette microcomputer 30 reads the identification memory chip 21 [201], wherein the cassette microcomputer 30 is programmed with the blister housing 20 information, such as the specific number of the plurality of blister housing compartments 22, and the shape and position of each of the plurality of blister housing compartments 22.

Figure 19:
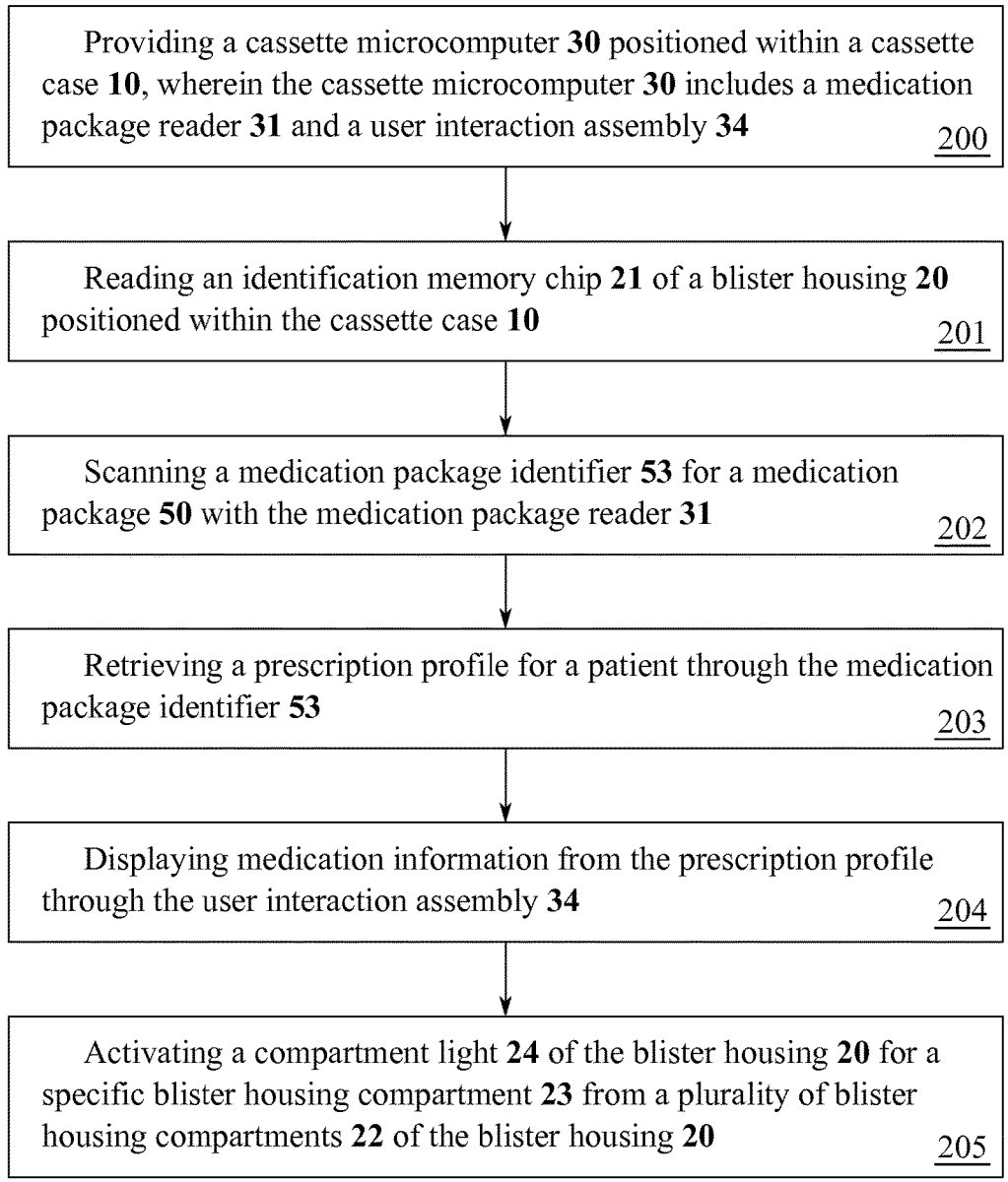
FIG. 19 is a flowchart depicting steps for administering the medication from the medication blister cassette.

In reference to FIG. 19, once the medication package 50 is positioned within the blister housing 20 and the cassette case 10, the medication package reader 31 scans the medication package identifier 53 [202] in order to retrieve the prescription profile [203]. If the medication package identifier 53 is the at least one scannable code 54, then the at least one camera 32 scans the at least one scannable code 54. If the medication package identifier 53 is the RFID tag 55, then the RFID reader 33 scans the RFID tag 55. Once the medication package reader 31 scans the medication package identifier 53, the cassette microcomputer 30 retrieves the prescription profile through the medication package identifier 53 in one of two ways.

Figure 20:
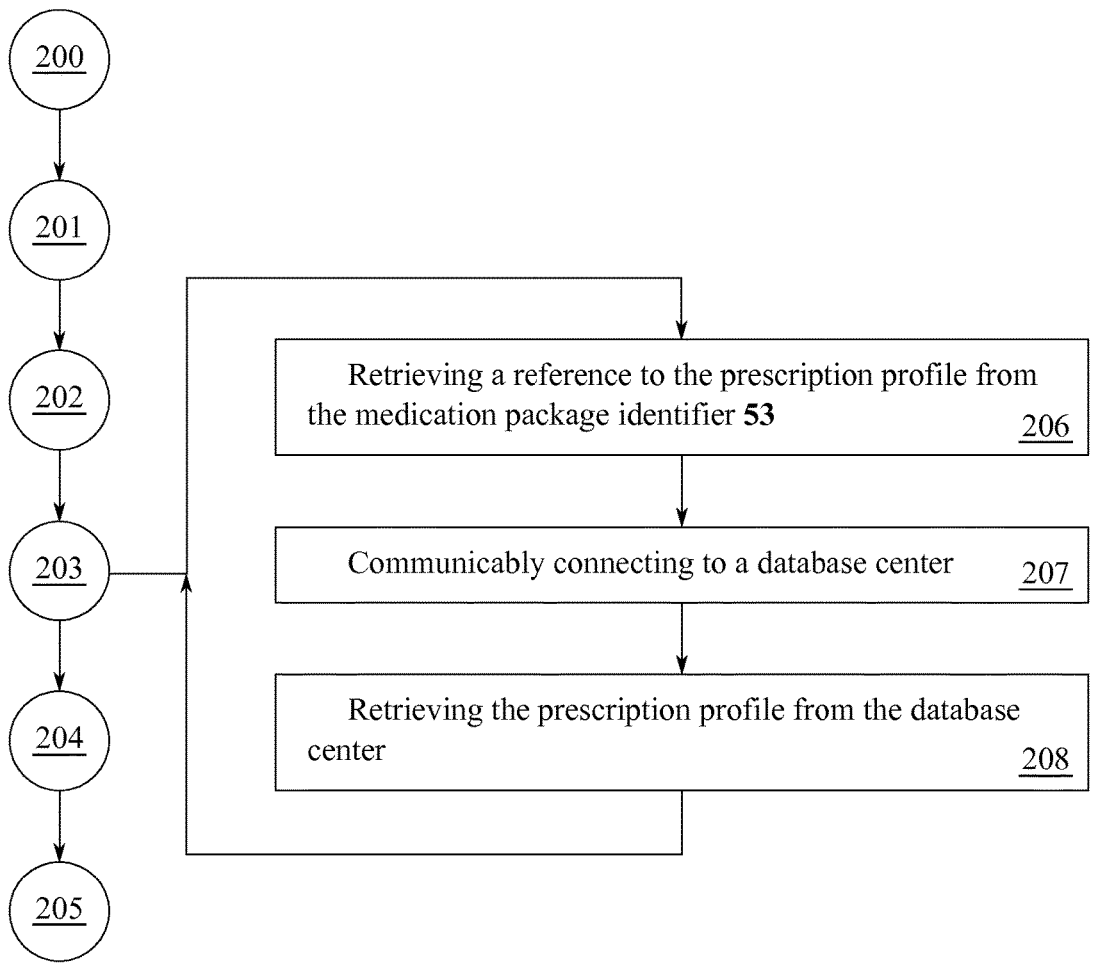
FIG. 20 is a flowchart thereof, further depicting steps for retrieving a prescription profile from a database center.

In one instance, a reference to the prescription profile is embedded in the medication package identifier 53, wherein the reference is used to retrieve the prescription profile from the database center. In reference to FIG. 20, the cassette microcomputer 30 retrieves the reference from the medication package identifier 53 [206] and then communicably connects to the database center [207]. Once connected to the database center, the cassette microcomputer 30 retrieves the prescription profile the database center and stores the prescription profile [208]. In another instance, the prescription profile is directly embedded in the medication package identifier 53, wherein the medication package reader 31 scans the medication package identifier 53 and the cassette microcomputer 30 retrieves the prescription profile from the medication package identifier 53 [203]. If the prescription profile embedded directly in the medication package identifier 53 does not contain all of the necessary information, then the cassette microcomputer 30 can connect to the database center in order to download additional prescription profile information.

If the medication package 50 does not include the medication package identifier 53, then the prescription profile can be retrieved using a prescription identification code. The prescription identification code is preferably a number, however, the prescription identification code can be any string of numbers, letters, or other symbols. The user enters the prescription identification code into the cassette microcomputer 30 through the user interaction assembly 34; either verbally dictated through the microphone 43, or entered though the display screen 40 or the additional control buttons 18. The cassette microcomputer 30 then communicably connects to the database center and retrieves the prescription profile. Additionally, the prescription identification code can be entered through the user computer, wherein the user computer either forwards the prescription identification code to the cassette microcomputer 30 or communicably connects to the database center, retrieves the prescription profile, and forwards the prescription profile to the cassette microcomputer 30.

In reference to FIG. 19, once the cassette microcomputer 30 has retrieved the prescription profile, the user can initiate the process of inspecting the medication package 50, wherein the medication information from the prescription profile is displayed through the user interaction assembly 34 [204]. The user initiates the process of inspecting the medication package 50 by first submitting a command to the cassette microcomputer 30 through the user interaction assembly 34. The medication information for the medication positioned within each of the plurality of blister housing compartments 22 is then displayed in sequence through the user interaction assembly 34.

Figure 21:
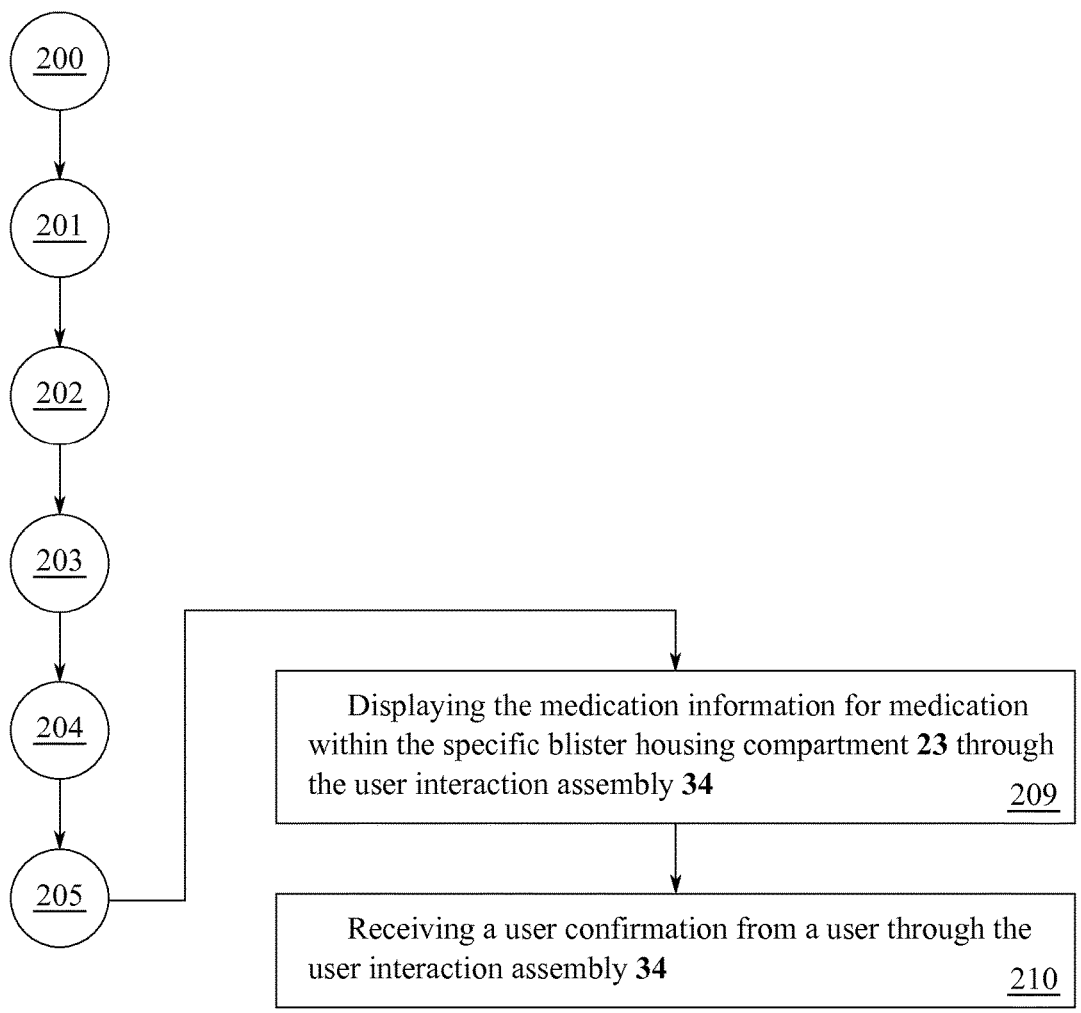
FIG. 21 is a flowchart thereof, further depicting steps for receiving a user confirmation for a particular action through a user interaction assembly.

In reference to FIG. 21, the cassette microcomputer 30 displays, through the display screen 40, the medication information for the medication in a specific blister housing compartment 23 from the plurality of blister housing compartments 22 [209]. Additionally, the cassette microcomputer 30 activates the compartment light 24 for the specific blister housing compartment 23 [205] in order to easily identify the specific blister housing compartment 23. The compartment light 24 only illuminates the specific blister housing compartment 23 (i.e. light does not leak through the blister housing 20 into the adjacent blister housing compartments) so that there is no confusion about the medication that should be administered from the plurality of blister housing compartments 22. The cassette microcomputer 30 then prompts the user to inspect the medication within the specific blister housing compartment 23 to ensure the medication matches that described in the medication information for the specific blister housing compartment 23. The user then provides a user confirmation, wherein the cassette microcomputer 30 receives the user confirmation through the user interaction assembly 34 [210].

Figure 22:
FIG. 22 is a flowchart thereof, further depicting steps for removing the medication package if medication information does not match the medication.
Figure 23:
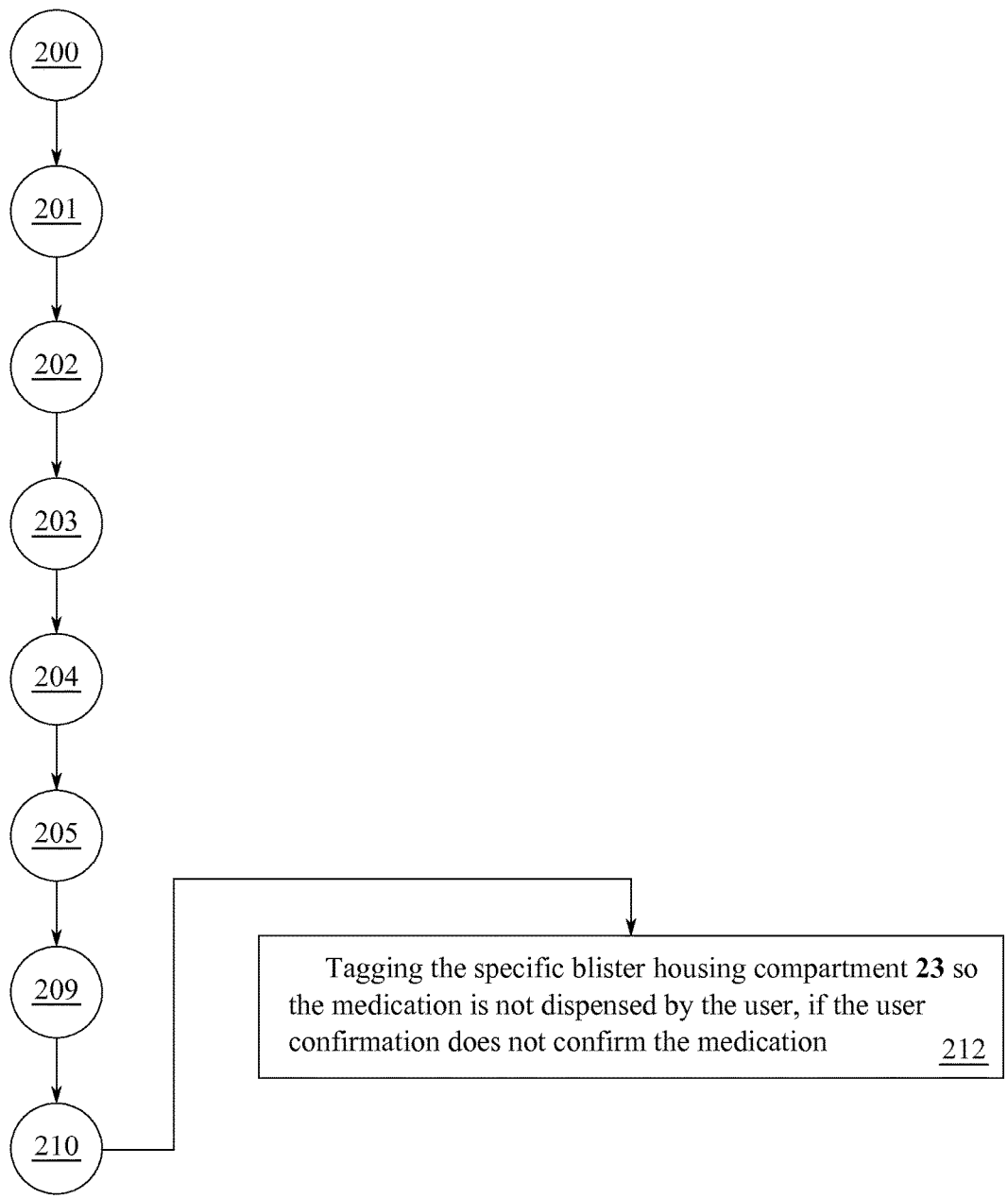
FIG. 23 is a flowchart thereof, further depicting steps for logging medication to not dispense if the medication information does not match the medication.

If the user confirmation confirms the medication in the specific blister housing compartment 23 with the medication information provided for the specific blister housing compartment 23, then the cassette microcomputer 30 checks if there are more blister housing 20 compartments to verify, and if so repeats the process for each of the remaining blister housing 20 compartments. If the user confirmation does not confirm the medication in the specific compartment with the medication information provided for the specific blister housing compartment 23, then the cassette microcomputer 30 asks the user if the user wants to reject the medication package 50. In reference to FIG. 22, the cassette microcomputer 30 then instructs the user through the user interaction assembly 34 to remove the medication package 50 if the user chooses to reject the medication package 50 [211]. In reference to FIG. 23, if the user chooses not to reject the medication package 50, then the cassette microcomputer 30 tags the specific blister housing compartment 23 as do not dispense [212], so that administration is not scheduled for the specific blister housing compartment 23 and the medication is not dispensed by the user at a later time.

The process for inspecting the medication package 50 can also be carried out using the user computer, wherein the process is initiated by the user on the user computer. The user submits the command to initiate the process for inspecting the medication package 50 to the user computer, wherein the medication information from the prescription profile is displayed on the user computer. If the prescription profile is not already stored on the user computer, then the user computer communicably connects to the cassette microcomputer 30 and downloads the prescription profile. The same process is then performed, wherein the compartment light 24 for the specific blister housing compartment 23 is activated; however, the user confirmation and all prompts to the user are processed through the user computer instead of the user interaction assembly 34.

Once the medication has been inspected by the user, the user can schedule the administration of the medication. Similar to the process for inspecting the medication, the user initiates the process for scheduling administration of the medication. The user initiates the process of scheduling administration of the medication by first submitting a command to the cassette microcomputer 30 through the user interaction assembly 34. A summary of the medication information from the prescription profile is then displayed through the user interaction assembly 34. Next, the user enters a medication start time for administering a first dose of the medication through the user interaction assembly 34.

Figure 27:
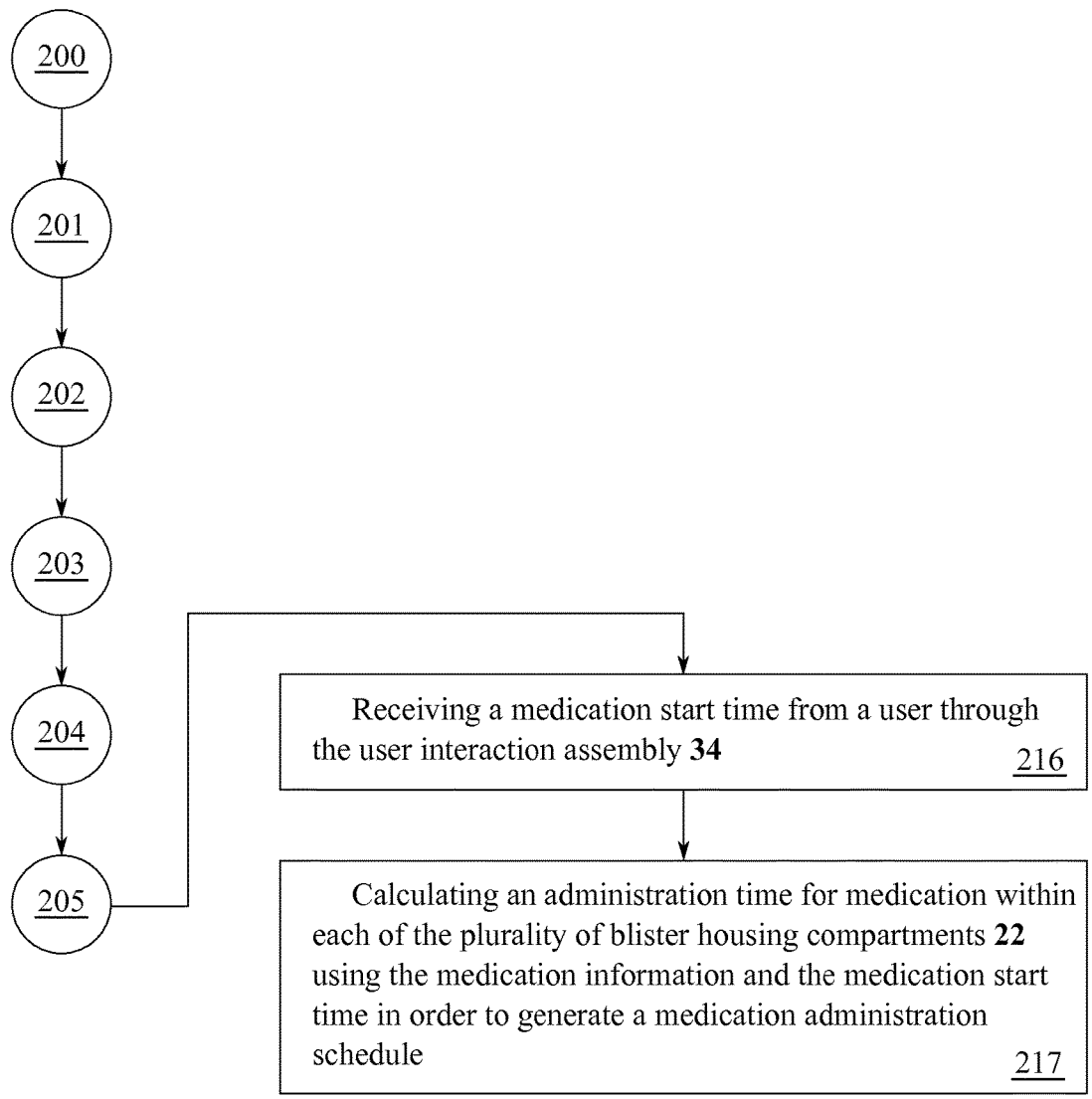
FIG. 27 is a flowchart thereof, further depicting steps generating a medication administration schedule used to notify the user of administration times.

In reference to FIG. 27, the cassette microcomputer 30 receives the medication start time through the user interaction assembly 34 [216] and calculates an administration time for the medication within each of the plurality of blister housing compartments 22 using the medication information and the medication start time [217]. The administration time for the medication within each of the plurality of blister housing compartments 22 is calculated in order to generate a medication administration schedule that is stored on the cassette microcomputer 30. For example, if the medication information dictates that the medication needs to be administered twice a day, eight hours apart, and the medication start time is Monday at ten in the morning, then the next dose would be scheduled at six in the afternoon and the schedule for Monday would be repeated until the number of doses of the medication package 50 is exhausted.

Figure 28:
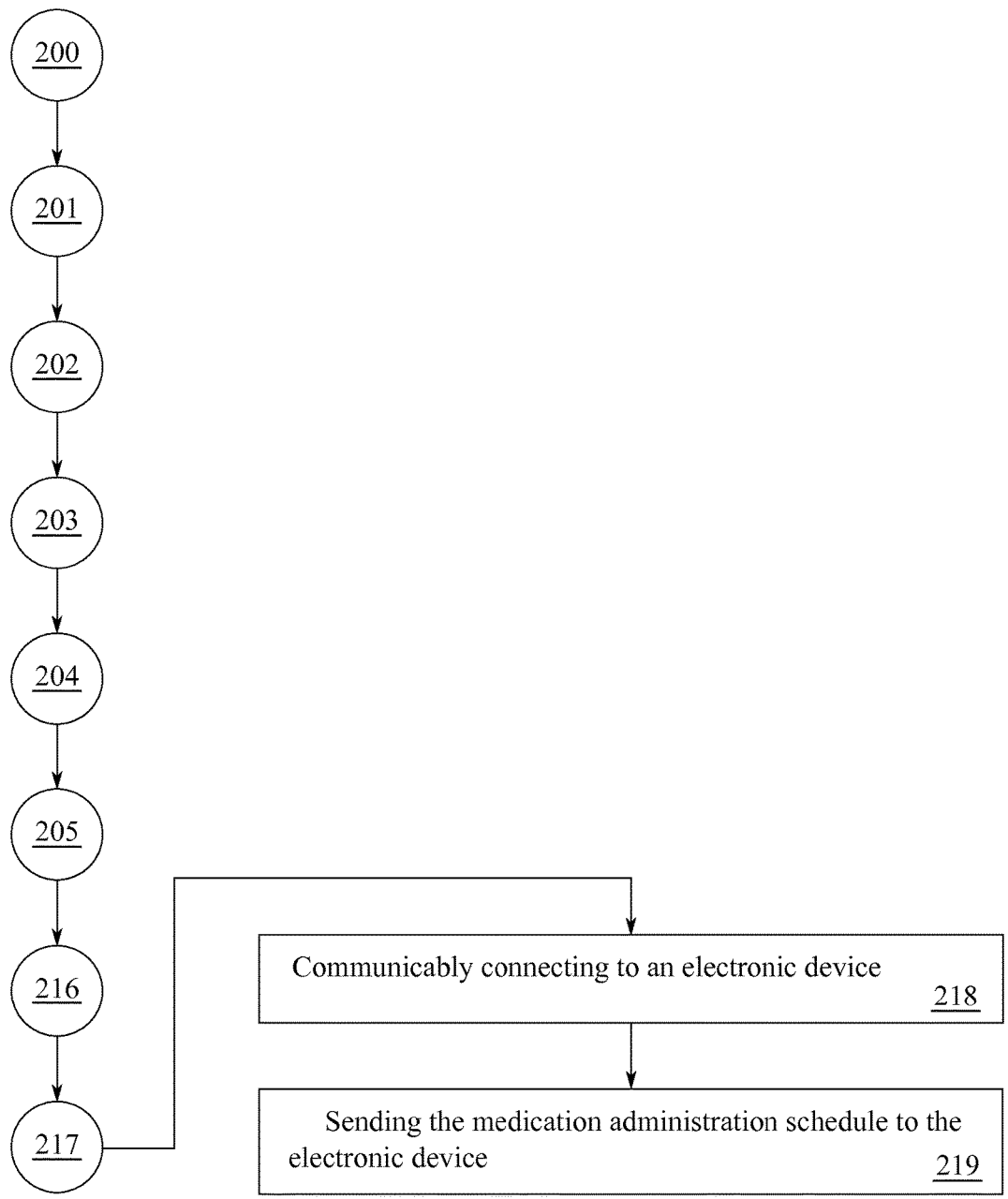
FIG. 28 is a flowchart thereof, further depicting steps for sharing the medication administration schedule with an electronic device communicably connected to the medication blister cassette.

For the administration time for the medication within each of the plurality of blister housing compartments 22, the user can either confirm the administration time, alter the administration time, or cancel the administration time. Once the medication administration schedule is finalized by the user, the medication administration schedule is then used to notify the user of when to administer the medication. In reference to FIG. 28, the medication administration schedule can also be shared with the user computer or the database center, wherein the cassette microcomputer 30 communicably connects to the electronic device [218] and sends the medication administration schedule to the electronic device [219]. The medication administration schedule is then stored locally on the electronic device, wherein the user computer or the database center can be utilized to send notifications to the user.

The process for scheduling administration of the medication can also be carried out using the user computer, wherein the process is initiated by the user on the user computer. The user submits the command to initiate the process for scheduling administration of the medication to the user computer, wherein the medication information from the prescription profile is displayed on the user computer. If the prescription profile is not already stored on the user computer, then the user computer communicably connects to the cassette microcomputer 30 and downloads the prescription profile. The medication start time is then entered into the user computer by the user, wherein the user computer calculates the administration time for the medication within each of the plurality of blister housing compartments 22 and generates the medication administration schedule. The medication administration schedule can then be altered by the user if necessary, and once finalized is stored on the user computer and sent to the cassette microcomputer 30 and optionally the database center.

The medication administration schedule is then used by the cassette microcomputer 30 to initiate the process for administering the medication, wherein the cassette microcomputer 30 schedules an alarm at the administration time for each dose of the medication. For the administration time of each dose of the medication, the cassette microcomputer 30 alerts the user by activating the alarm. Any number of methods may be used to alert the user including, but not limited to, the following means: an audio alert, such as an alarm and/or instructions, through the speaker 41; a visual alert by activating the compartment light 24 for the specific blister housing 20; a visual alert by activating the display screen 40; a physical alert using the vibrator 42; an audio alert through the user computer; a visual alert through the user computer; a physical alert by vibrating the user computer; a visual or audio alert through another device synchronized with the medication blister cassette 1, such as a lighting fixture; or a combination thereof.

Once alerted, the user can continue the process for administering the medication by submitting a command through the user interaction assembly 34, or otherwise acknowledging the alarm. The cassette microcomputer 30 then displays the medication information for the specific blister housing compartment 23 [209] and activates the compartment light 24 for the specific blister housing compartment 23 [205]. Next, the cassette microcomputer 30 prompts the user to confirm the administration of the medication. The user then submits a user confirmation for the administration of the medication, wherein the cassette microcomputer 30 receives the user confirmation for the administration of the medication through the user interaction assembly 34 [210].

Figure 24:
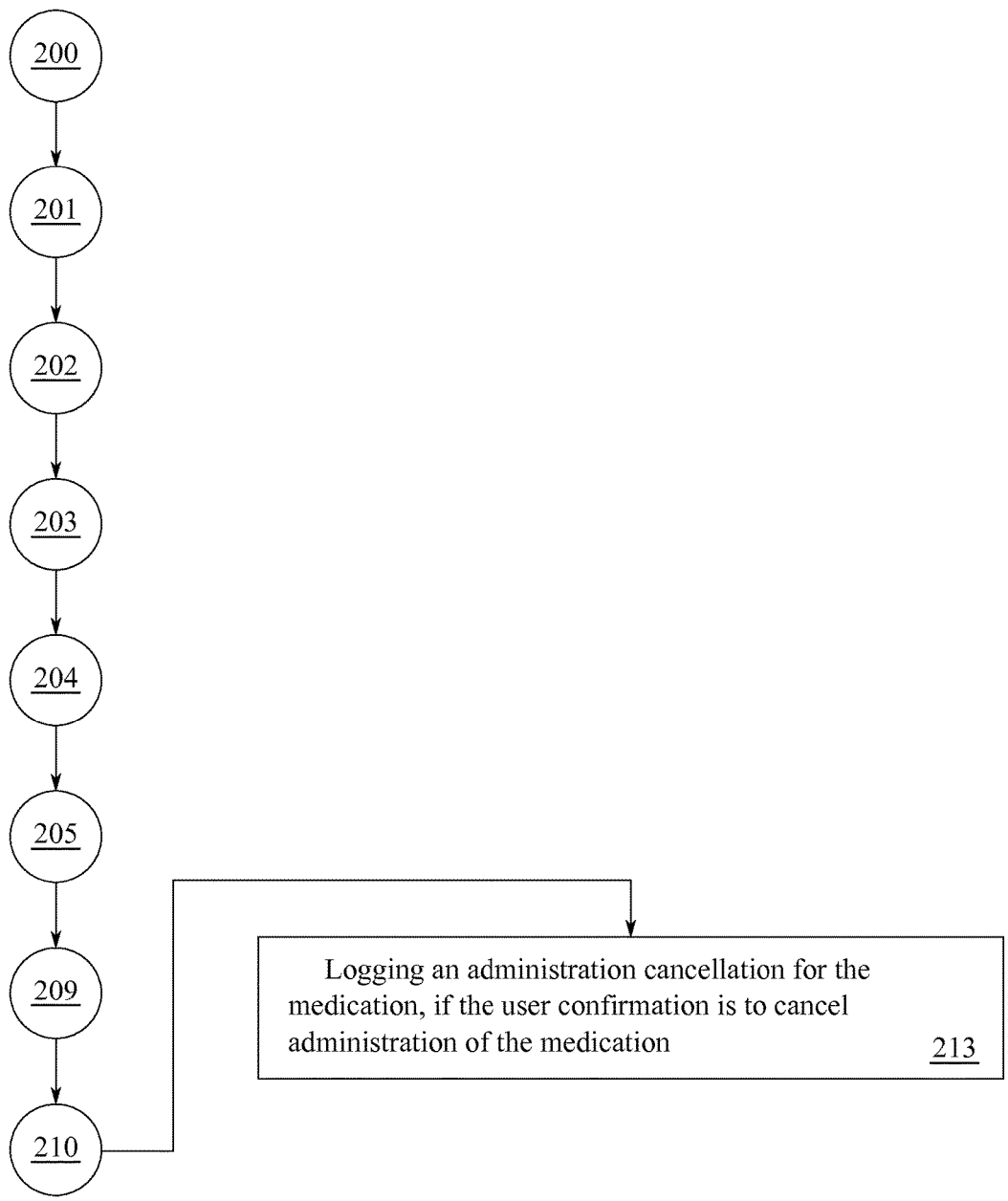
FIG. 24 is a flowchart thereof, further depicting steps for logging an administration cancellation if a user cancels administration of the medication.
Figure 25:
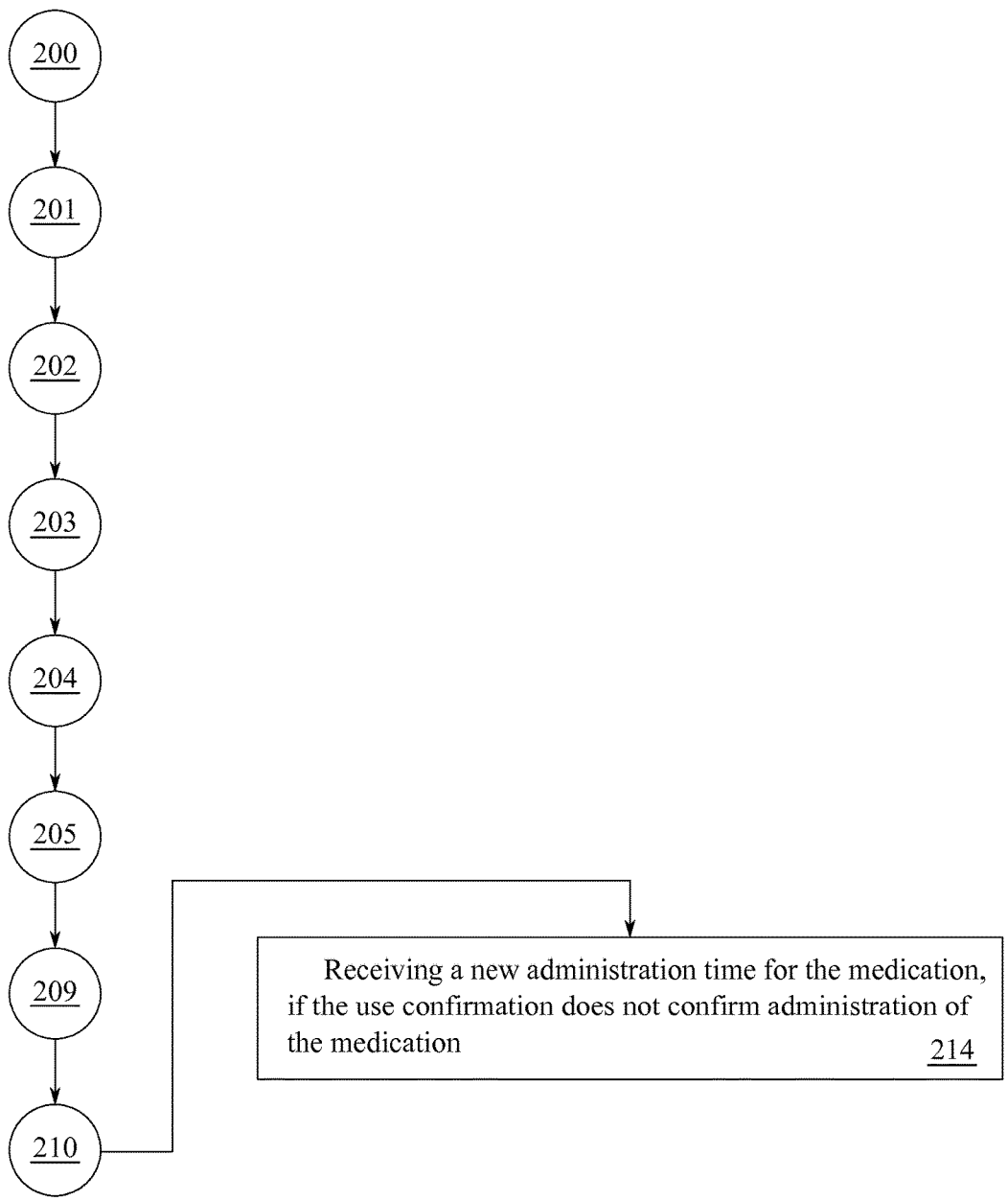
FIG. 25 is a flowchart thereof, further depicting steps for rescheduling the administration of a dose of the medication.
Figure 26:
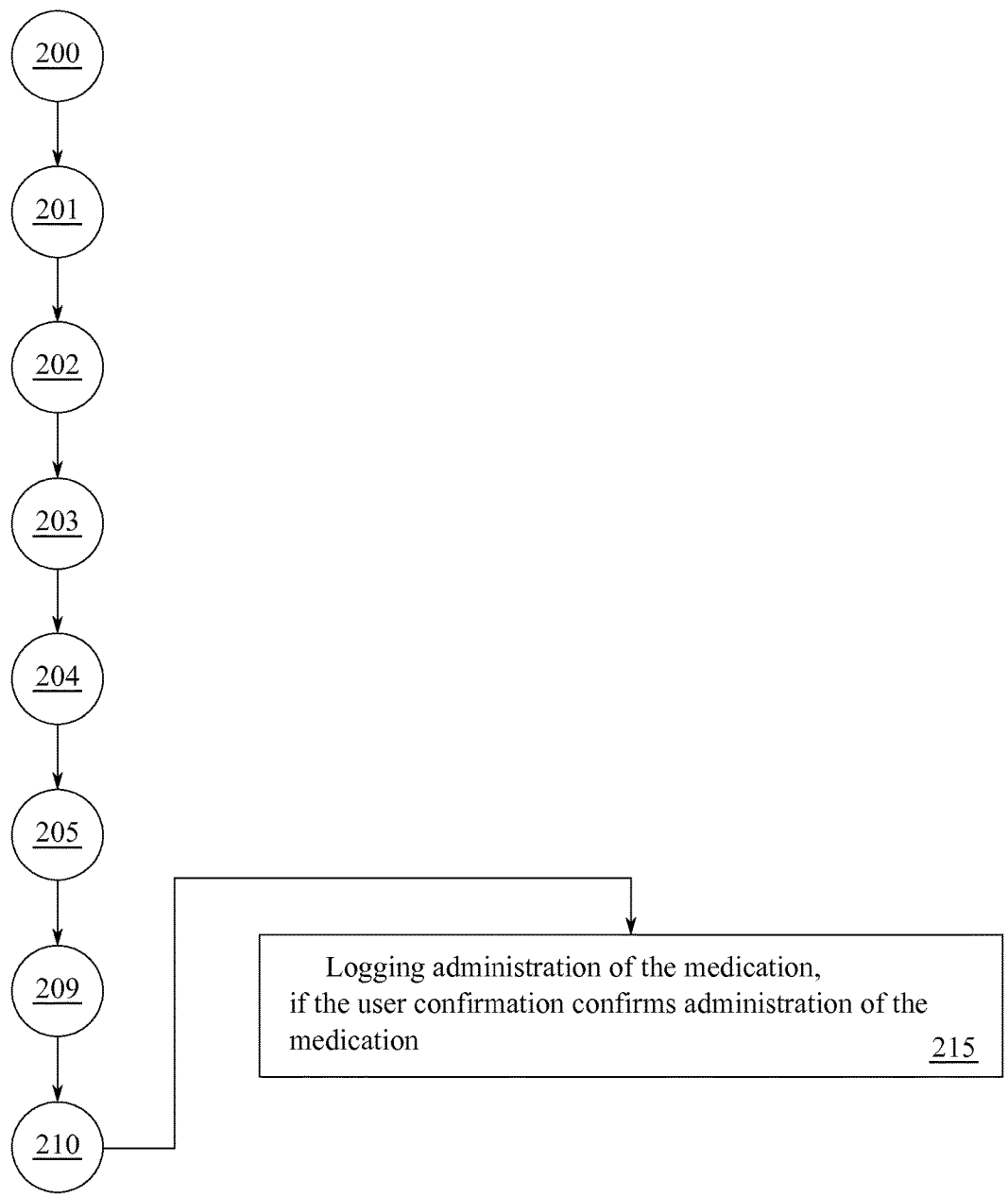
FIG. 26 is a flowchart thereof, further depicting steps for logging administration of the medication if the user confirms administration.

In reference to FIG. 26, if the user chooses to administer the medication, then the user confirmation for the administration of the medication confirms the administration of the medication and the cassette microcomputer 30 logs the administration of the medication [215]. In reference to FIG. 24-25, the user may also choose to cancel or reschedule the administration of the medication, wherein the user confirmation for the administration of the medication does not confirm the administration of the medication. If the administration of the medication is cancelled, then the cassette microcomputer 30 logs an administration cancellation for the medication in the specific blister housing compartment 23 [213]. If the administration of the medication is rescheduled, then the cassette microcomputer 30 receives a new administration time for the medication in the specific blister housing 20 from the user through the user interaction assembly 34 [214]; the cassette microcomputer 30 then creates a new alarm according to the new administration time. For whichever option is chosen by the user, the activity of the user is recorded and optionally shared with the user computer or the database center.

The user can also continue the process for administering the medication by submitting a command through the user computer. If the prescription profile is not already stored on the user computer, then the user computer communicably connects to the cassette microcomputer 30 and downloads the prescription profile. The user computer then displays the medication information for the specific blister housing compartment 23 and the compartment light 24 for the specific blister housing compartment 23 is activated by the cassette microcomputer 30. Next, the user computer prompts the user to confirm the administration of the medication, wherein the user then submits the user confirmation for the administration of the medication through the user computer. The activity of the user is logged on the user computer and can then be shared with the cassette microcomputer 30 or the database center.

The medication blister cassette 1 can also be used to administer the medication without generating the medication administration schedule. In such a case, the process for administering the medication is initiated by the user, wherein the user enters the specific blister housing compartment 23 for the medication that is to be administered into the cassette microcomputer 30 through the user interaction assembly 34. The cassette microcomputer 30 then displays the medication information for the medication and checks the administration history for the medication. If there is a clinical issue with administering the medication, then the cassette microcomputer 30 warns the user through the user interaction assembly 34, wherein the user can choose whether or not to override the system. If the user overrides the system or if there is no warning issued, then the cassette microcomputer 30 activates the compartment light 24 for the specific blister housing compartment 23. In any case, the activity of the user is logged by the cassette microcomputer 30 and may be shared with the user computer or the database center.

The user computer can also be used to administer the medication without generating the medication administration schedule. In such a case, the process for administering the medication is initiated by the user, wherein the user enters the specific blister housing compartment 23 for the medication that is to be administered into the user computer. If the prescription profile is not already stored on the user computer, then the user computer communicably connects to the cassette microcomputer 30 and downloads the prescription profile. The user computer then displays the medication information for the medication and checks the administration history for the medication. If there is a clinical issue with administering the medication, then the user computer warns the user, wherein the user can choose whether or not to override the system. If the user overrides the system or if there is no warning issued, then the cassette microcomputer 30 activates the compartment light 24 for the specific blister housing compartment 23. In any case, the activity of the user is logged by the user computer and may be shared with the cassette microcomputer 30 or the database center.

In one embodiment of the present invention, the medication blister cassette 1 automatically records administration of the medication by interacting with the medication package 50 being a smart medication package 50. The smart medication package 50 has a plurality of sensors capable of monitoring the plurality of blisters 51. Each of the plurality of sensors monitors a specific blister from the plurality of blisters 51 and can recognize whether or not the specific blister has been opened. The plurality of sensors is electronically connected to the cassette microcomputer 30 through a wired connection.

In another embodiment of the present invention, the medication blister cassette 1 automatically records administration of the medication by interacting with the blister housing 20. The blister housing 20 further comprises an optical sensor for each of the plurality of blister housing compartments 22, wherein the optical sensor can recognize whether or not the specific blister has been opened. The optical sensor for each of the plurality of blister housing compartments 22 is electronically connected to the cassette microcomputer 30 through a wired connection.

In yet another embodiment of the present invention, the medication blister cassette 1 automatically verifies the medication package and records administration of the medication using a picture of the medication package 50. The medication package 50 comprises a medication housing color pattern, a perimeter mark, and a plurality of color code marks. The medication housing color pattern is a colored background behind the plurality of blisters 51, used to contrast with the medication within the plurality of blisters 51. The perimeter mark is used to align images taken of the medication package 50, while the plurality of color code marks are used to compare images taken in environments with different lighting. Together, the medication housing color pattern, the perimeter mark, and the plurality of color code marks are used to generate package image matrices of the medication package 50, which are then used to verify the medication in the plurality of blisters 51. The picture of the medication package 50 can be taken using the at least one camera 32 or a subsequent camera integrated into the cassette case 10, or through a camera of the user computer. The system then utilizes computer vision processes and methods to visually analyze the medication package 50 in order to determine opened blisters. The visual analysis can be performed on the cassette microcomputer 30, the user computer, the database center, or a combination thereof.

The medication blister cassette 1 retrieves a manufacturer package image matrix consisting of visual characteristics of the medication package 50 from the prescription profile. Provided the medication package 50, a patient or caregiver receives the medication package 50 and then uses the medication blister cassette 1 to obtain a captured image of the medication package 50. The captured image is stored on the medication blister cassette 1. Upon receiving the captured image, the medication blister cassette 1 analyzes the captured image in order to generate a current package image matrix. By analyzing the captured image, the medication blister cassette 1 generates the current package image matrix from visual characteristics of the medication package; specifically by identifying a current medication housing color pattern, current medication colorings, a plurality of current color code marks, and a current perimeter mark from the captured image. The medication blister cassette 1 uses the current medication housing color pattern, the current medication colorings, the plurality of current color code marks, and the current perimeter mark to graphically organize the current package image matrix from the captured image.

The current perimeter mark is used to align the captured image, if the medication package 50 is askew in the captured image. Additionally, the current perimeter mark may be used to crop the captured image. Once the captured image is aligned properly, the current medication housing color pattern and the current medication colorings are compared to the plurality of current color code marks in order to generate a current color-contrast reference. The current color-contrast reference is then used to calculate a current number of empty blisters by measuring the light contrast about each of the plurality of medication housing indicators. The current color-contrast reference is also used to identify current empty blister locations of the plurality of blisters in order to determine if a dose of the prescribed medication has been improperly administered. Each of the plurality of blisters is then identified in the current package image matrix with a mark to indicate whether or not the medication within has been administered. The same process can also be used to determine a current number of filled medication pockets and current filled blister locations if desired. The medication blister cassette 1 then compares the current package image matrix to the manufacturer package image matrix in order to validate the current package image matrix with the manufacturer package image matrix. This ensures that the medication package 50 is not defective, has not been tampered with, etc.

Provided the current number of empty medication blisters and an initial number of empty medication blisters and provided the current empty blister locations and initial empty blister locations; the current package image matrix is validated with the manufacturer package image matrix by comparing the initial number of empty medication blisters to the current number of empty medication blisters and by comparing the initial empty blister locations to the current empty blister locations. The initial number of empty medication blisters is compared to the current number of empty medication blisters in order to validate the current number of empty medication blisters with the initial number of empty medication blisters. The current number of empty medication blisters must match the initial number of empty medication blisters in order to validate the current number of empty medication blisters. Similarly, the initial empty blister locations is compared to the current empty blister locations in order to validate the current empty blister locations with the initial empty blister locations. The current empty blister locations must match the initial empty blister locations in order to validate the current number of empty medication blisters. This process can also be used to verify the administration of each dose of the medication by creating a subsequent package image matrix each time the medication is administered, and then comparing the subsequent package image matrix to a previous package image matrix.

Figure 32:
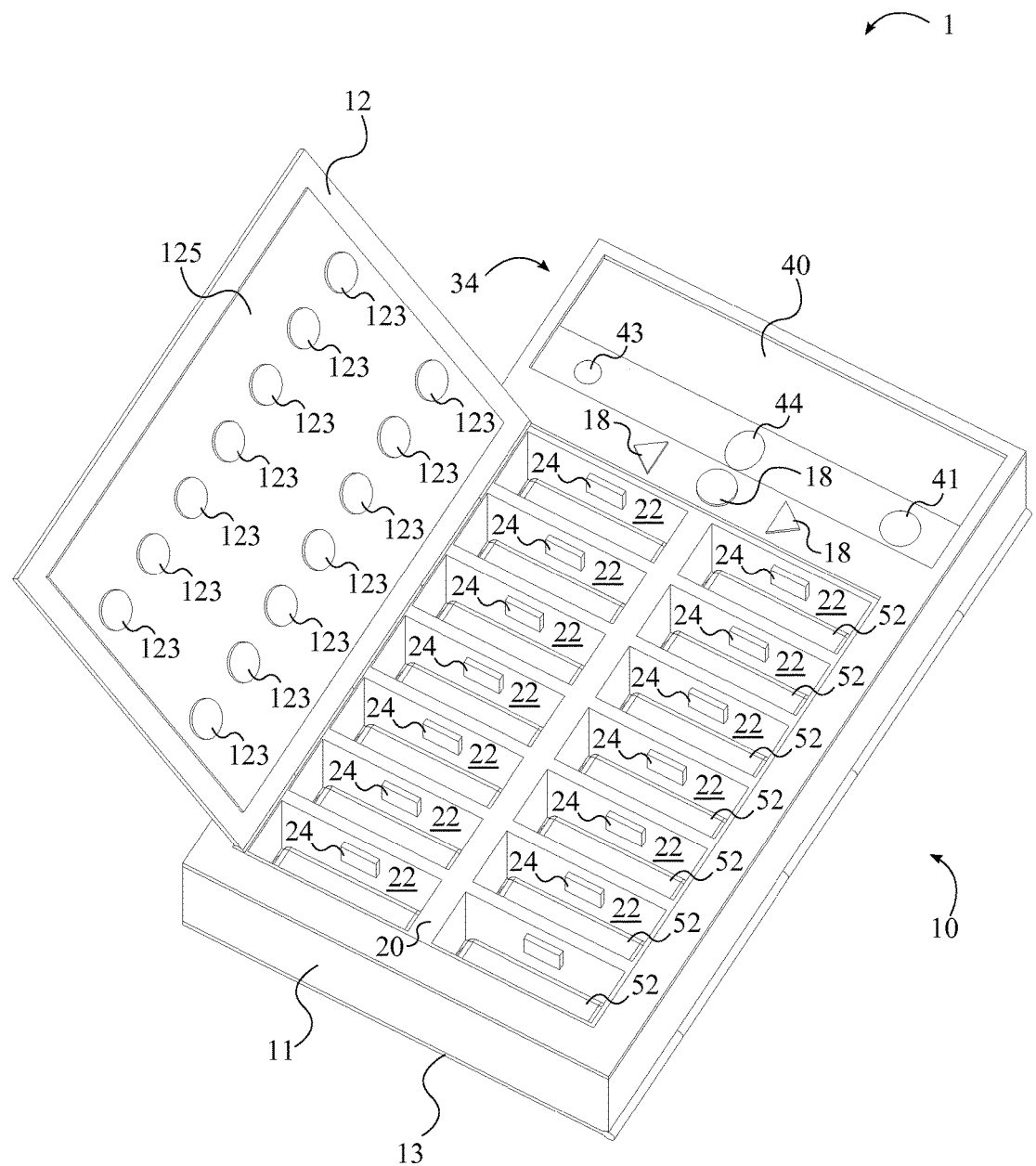
FIG. 32 is a perspective view of the medication blister cassette, wherein the first cover comprises a computer vision microcontroller and a plurality of medication monitors.
Figure 33:
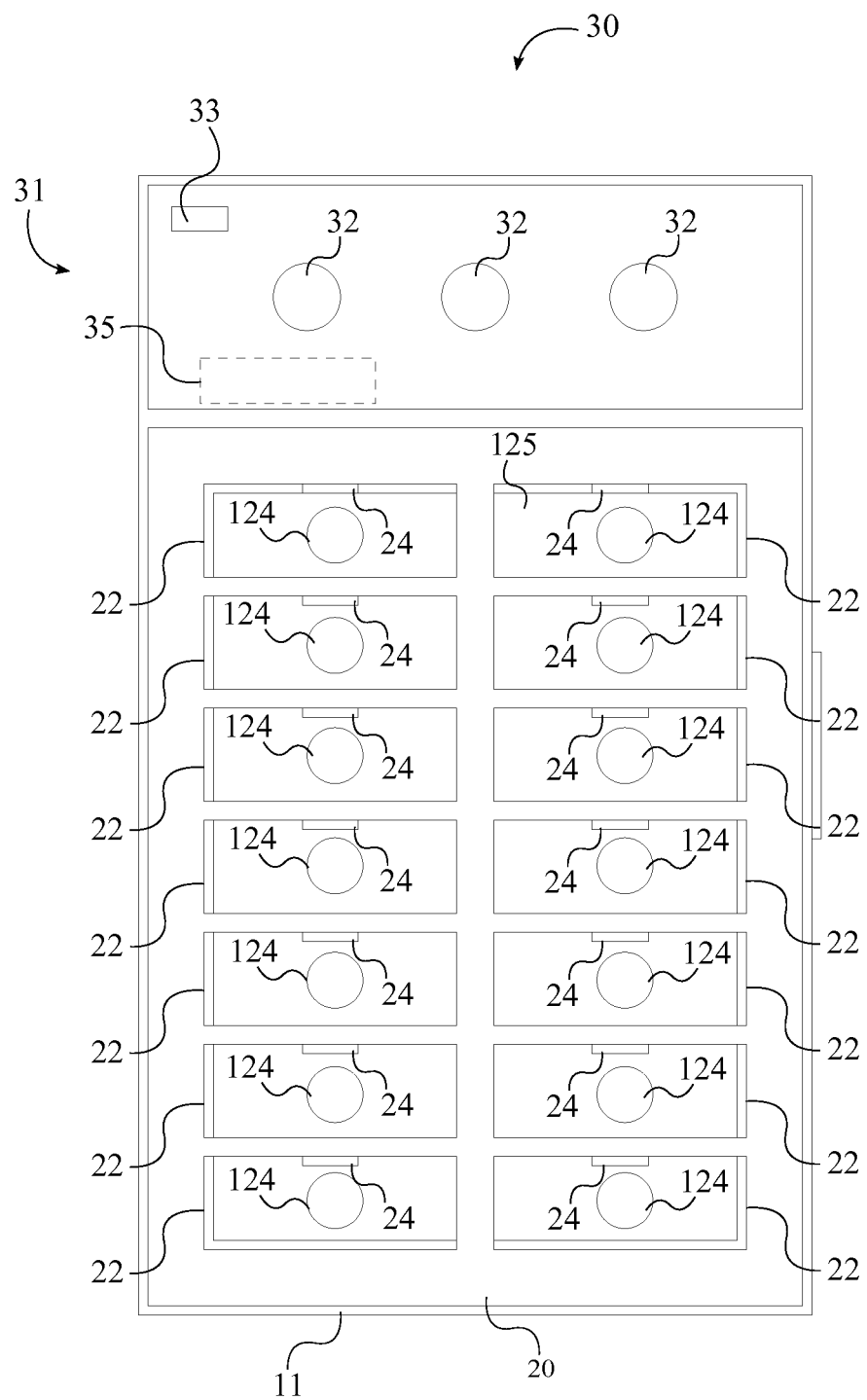
FIG. 33 is a bottom sectional view of the cassette microcontroller showing the specific medication monitor from the plurality of medication monitors being positioned adjacent to each of the plurality of blister housing compartments.

In reference to FIG. 32-33, in one embodiment of the present invention, the first cover 12 comprises a plurality of medication monitors 123 and a computer vision microcontroller 125. The plurality of medication monitors 123 is positioned about the first cover 12, such that each of the plurality of blister housing compartments 22 is positioned adjacent to a specific medication monitor 124 from the plurality of medication monitors 123 when the first cover 12 is closed, wherein each of the plurality of medication monitors 123 is used to detect whether or not the medication in the specific blister housing compartment 23 has been administered. The specific medication monitor 124 scans only the specific blister housing compartment 23 in order to determine whether or not the medication has or has not been administered from the specific blister housing compartment 23. The plurality of medication monitors 123 is electronically connected to the computer vision microcontroller 125, wherein the computer vision microcontroller 125 aggregates a signal or image from each of the plurality of medication monitors 123. The aggregated signal or image is then relayed to the cassette microcomputer 30 in order to determine whether or not the medication has been administered. As such, the computer vision microcontroller 125 is electronically connected to the cassette microcomputer 30 in addition to the plurality of medication monitors 123. Each of the plurality of medication monitors 123 can be an infrared sensor, a camera, or another type of device capable of detecting the presence or absence of the medication within the plurality of blister housing compartments 22.

Figure 30:
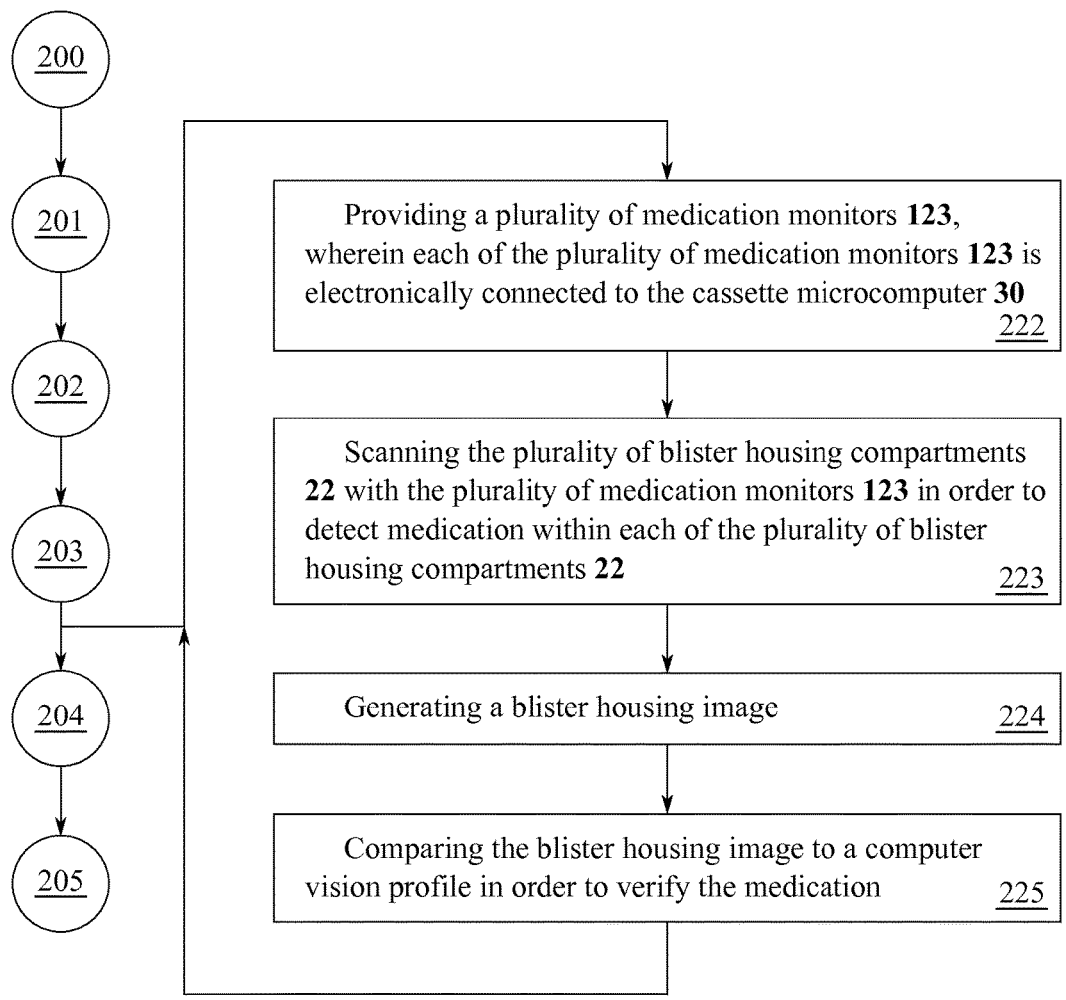
FIG. 30 is a flowchart thereof, further depicting steps for verifying the medication package using the plurality of medication monitors.

The computer vision microcontroller 125 and the plurality of medication monitors 123 can be used to initially verify the medication, as well as automatically log administration of doses of the medication. In reference to FIG. 30, in order to initially verify the medication, when the medication package 50 is positioned into the blister housing 20 and the first cover 12 is closed, the medication blister cassette 1 scans the plurality of blister housing compartments 22 with the plurality of medication monitors 123 in order to detect the medication within each of the plurality of blister housing compartments 22 [223]. The cassette microcomputer 30 then generates a blister housing image [224] using the aggregated signal or image of each of the plurality of medication monitors 123. Once the blister housing image is created, the cassette microcomputer 30 compares the blister housing image to a computer vision profile in order to verify the medication [225]. The computer vision profile is a similar aggregate signal or image that is taken when the medication package 50 is manufactured. In this way, by comparing the computer vision profile created at the time of manufacture to the blister housing image generated through the plurality of medication monitors 123, the cassette microcomputer 30 can determine whether or not the medication package 50 has been tampered with or if any of the medication is missing.

Figure 31:
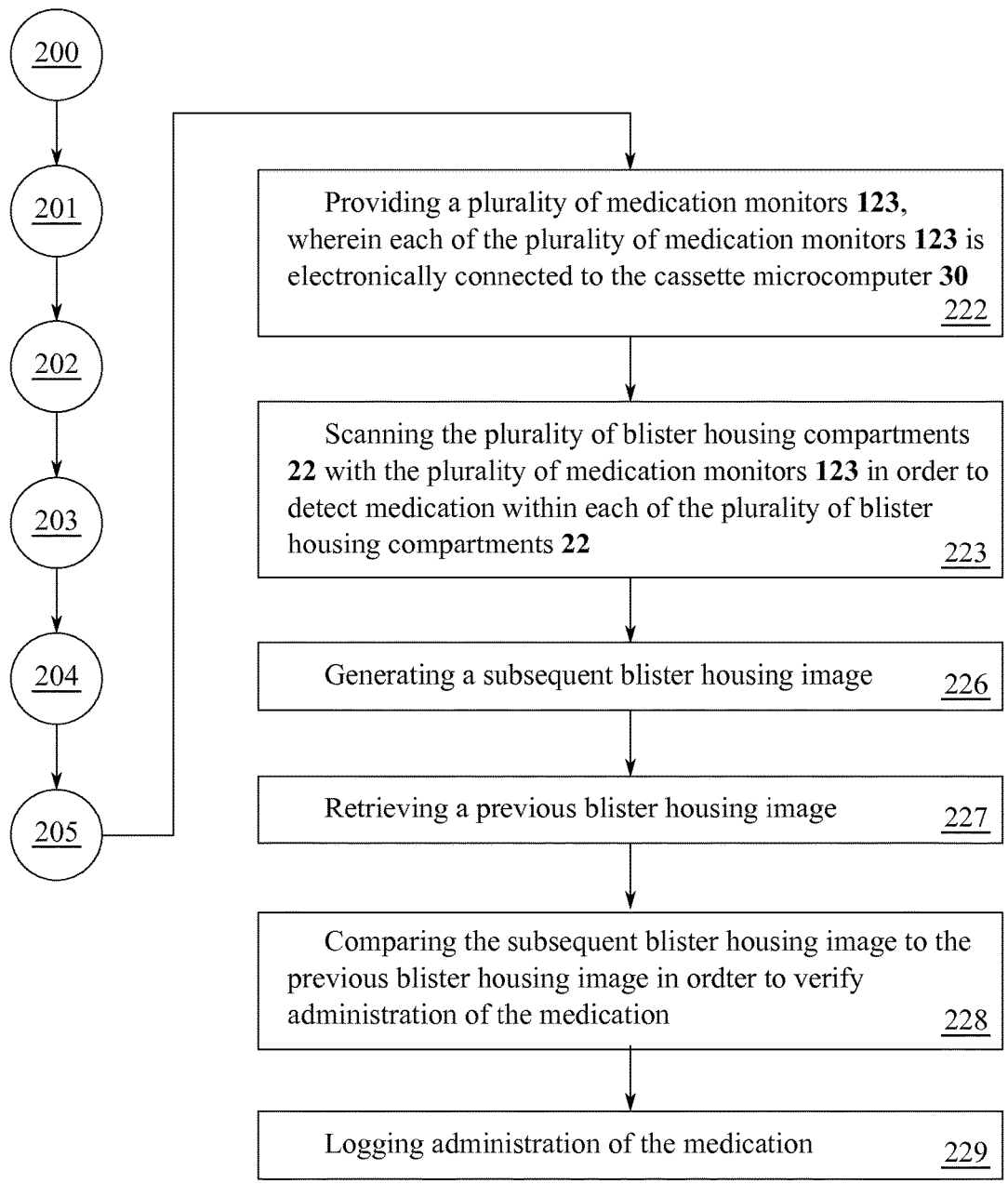
FIG. 31 is a flowchart thereof, further depicting steps for verifying the administration of a dose of the medication using the plurality of medication monitors.

A similar method can also be used to automatically log administration of the medication. In reference to FIG. 31, after the user administers the medication from the specific blister housing compartment 23 and closes the first cover 12, the medication blister cassette 1 scans the plurality of blister housing compartments 22 with the plurality of medication monitors 123 [223] and the cassette microcomputer 30 generates a subsequent blister housing image [226]. The cassette microcomputer 30 then retrieves a previous blister housing image [227] and compares the subsequent blister housing image to the previous blister housing image in order to verify the administration of the medication [228]. For example, after the first dose of medication is administered, the blister housing image used to initially verify the medication is used as the previous blister housing image, wherein the blister housing image shows the medication package 50 being full; the cassette microcomputer 30 then compares the subsequent blister housing image to the blister housing image in order to identify the specific blister housing compartment 23 from which the medication was administered. The cassette microcomputer 30 then logs the administration of the medication for future reference [229].

Figure 29:
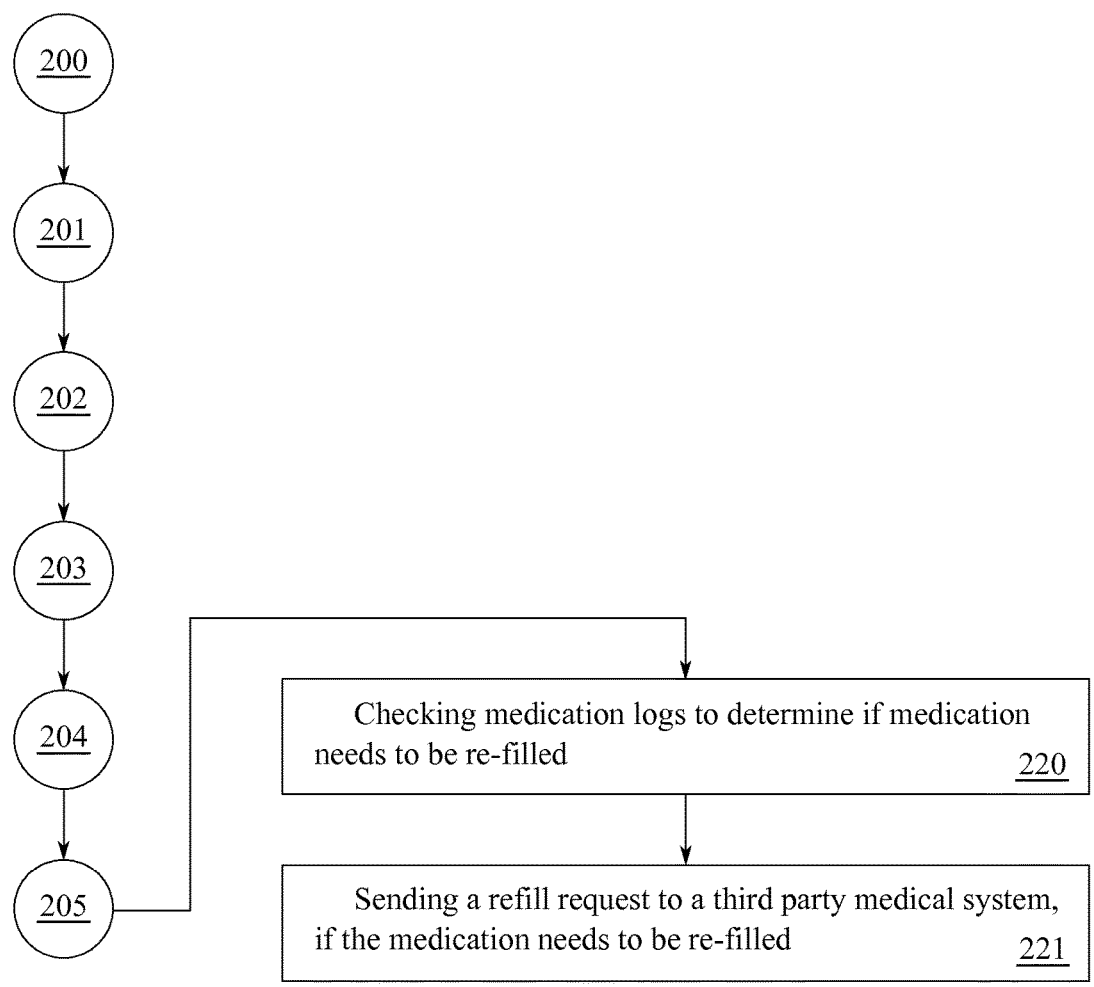
FIG. 29 is a flowchart thereof, further depicting steps for checking medication logs to determine whether or not the medication needs to be re-filled.

In reference to FIG. 29, each time the medication is administered, the cassette microcomputer 30 checks medication logs to determine if the medication needs to be re-filled [220]. If the medication needs to be re-filled, then the cassette microcomputer 30 sends a refill request to a third party medical system [221]. The third party medical system to which the refill request is sent depends on whether or not the prescription profile contains an authorization for ordering a medication refill. If the prescription profile contains the authorization for ordering the medication refill, then the cassette microcomputer 30 sends the refill request directly to a pharmacy. If the prescription profile does not contain the authorization for ordering the medication refill, then the cassette microcomputer 30 sends the refill request to a doctor, wherein the doctor can send the authorization to the pharmacy or back to the cassette microcomputer 30.

If the medication package 50 is empty, then the cassette microcomputer 30 instructs the user to remove the medication package 50 from the cassette case 10. The cassette microcomputer 30 then checks the prescription profile to determine whether or not the user needs to continue administering the medication, and if so instructs the user to insert a subsequent medication package 50. If the medication package 50 is removed before all of the medication is administered, then the cassette microcomputer 30 checks the prescription profile to verify whether or not the user is supposed to continue therapy with the medication. If the prescription profile indicates that the user is to continue therapy with the medication, then the cassette microcomputer 30 instructs the user to reinsert the medication package 50 into the cassette case 10.

As previously stated, the medication blister can be used standalone or with the user computer or the database center; information can be stored directly on the cassette microcomputer 30 or shared amongst the devices. In addition to the user computer and the database center, the medication blister cassette 1 can be communicably connected to other electronic devices of pharmacies, doctors, and drug manufacturers. In this way, advisory messages from pharmacies, doctors, or drug manufacturers in regards to the medication can be sent directly to the user through the medication blister cassette 1. The user can then use the medication blister cassette 1 to acknowledge the advisories or other messages, as well as send follow-up questions directly to the pharmacies, doctors, or drug manufacturers.

The ability to connect to other electronic devices also allows the medication blister cassette 1 to communicate with a designated caregiver (e.g. family member), physician, or pharmacist if necessary. Some instances in particular include the user ignoring the alarm and not acknowledging administration of the medication, the user cancelling administration of the medication, or the administration of a dose that was cancelled by the doctor or pharmacy. In such a case, the medication blister cassette 1 can communicate with the electronic device of the caregiver, physician, pharmacist, etc., such that the proper authorities can check on the user.

Furthermore, the ability to connect to other electronic devices allows the user to consult with caregivers, physicians, pharmacists, etc. through the medication blister cassette 1. If the user has a particularly important question or is in an emergency situation, the user can send out a message directly to the electronic device of the caregiver, physician, pharmacist, etc., through the medication blister cassette 1. The diverse functionality of the user interaction assembly 34 is particularly beneficial in emergency situations, as the user may be disabled or incapacitated, thus preventing them from communicating in a particular manner.

The use of a plurality of medication blister cassettes can also be beneficial in healthcare institutions as part of a medication inventory management system. In such an instance, the plurality of medication blister cassettes can be used to control the administration of medications to multiple patients, wherein only authorized personnel have access to the plurality of medication blister cassettes. This also provides increased protection to prevent theft as all activities are logged on the plurality of medication blister cassettes and only authorized personnel have access to the plurality of medication blister cassettes. Furthermore, utilizing the plurality of medication blister cassettes would lend to maintaining the medication inventory of the medical institution, as each of the plurality of medication blister cassettes can be communicably connected to the network of the medical institution and share information in regards to the distribution of medications to patients.

Although the invention has been explained in relation to its preferred embodiment, it is to be understood that many other possible modifications and variations can be made without departing from the spirit and scope of the invention as hereinafter claimed.

What is claimed is:

1. A medication blister cassette system comprising:
   a cassette case;
   a blister housing;
   a cassette microcomputer;
   a medication package;
   a computer vision microcontroller;
   a plurality of medication monitors;
   the cassette case comprising a lateral cassette wall, a first cover, a second cover and a third cover;
   the first cover and the second cover each being connected to the lateral cassette wall;
   the first cover and the second cover being oppositely located to each other about the lateral cassette wall;
   the first cover comprising a first opening and a second opening;
   the first opening and the second opening being separate from each other;
   the second cover comprising a first aperture and a second aperture;
   the first aperture and the second aperture being separate from each other;
   the third cover being rotatably connected to the first cover;
   the third cover being adjacently located to the first opening;
   the third cover having a closed position and an open position;
   the first opening being covered by the third cover in response to the third cover being rotated to the closed position;
   the first opening being not covered by the third cover in response to the third cover being rotated to the open position;
   the blister housing being accommodated within the cassette case;
   the blister housing comprising a plurality of blister housing compartments;
   the plurality of blister housing compartments being separate from each other;
   the plurality of blister housing compartments being adjacently located to the first opening;
   the plurality of blister housing compartments being not visually exposed through the first opening in response to the first opening being covered by the third cover:
   the plurality of blister housing compartments being visually exposed through the first opening in response to the first opening being not covered by the third cover;
   the cassette microcomputer being accommodated within the cassette case;
   the medication package being accommodated within the cassette case;
   the medication package comprising a plurality of blisters and a prescription labeling;
   the plurality of blisters being separate from each other;
   a corresponding blister among the plurality of blisters being accommodated within a corresponding blister housing compartment among the plurality of blister housing compartments;
   the plurality of blisters being adjacently located to the first aperture;
   the plurality of blisters being visually exposed through the first aperture in response to a corresponding blister among the plurality of blisters being accommodated within a corresponding blister housing compartment among the plurality of blister housing compartments;
   the prescription labeling being adjacently located to the second aperture;
   the prescription labeling being visually exposed through the second aperture;
   the computer vision microcontroller being externally connected to the third cover;
   the computer vision microcontroller being adjacently located to the first opening and being located in between the third cover and the plurality of blister housing compartments in response to the first opening being covered by the third cover;
   the plurality of medication monitors being connected to the computer vision microcontroller;
   the computer vision microcontroller being connected in between the third cover and the plurality of medication monitors;
   a corresponding medication monitor among the plurality of medication monitors being adjacently located to a corresponding blister housing compartment among the plurality of blister housing compartments in response to the computer vision microcontroller being adjacently located to the first opening and being located in between the third cover and the plurality of blister housing compartments; and
   the cassette microcomputer, the computer vision microcontroller and the plurality of medication monitors being electronically connected to each other.

2. The medication blister cassette system as claimed in claim 1 comprising:
   the cassette case comprising a first child lock; and
   the first child lock engaging the first cover with the lateral cassette wall.

3. The medication blister cassette system as claimed in claim 1 comprising:
   the cassette case comprising a first cover sensor;
   the first cover sensor being positioned adjacent to the first cover; and
   the first cover sensor being electronically connected to the cassette microcomputer.

4. The medication blister cassette system as claimed in claim 1 comprising:

the blister housing comprising an identification memory chip;

the identification memory chip being electronically connected to the cassette microcomputer;

the cassette microcomputer comprising a user interaction assembly and a transceiver;

the user interaction assembly being accessible through the first cover;

a portion of the user interaction assembly being visually exposed through the second opening; and the transceiver being configured to wirelessly communicate with an electronic device.

5. The medication blister cassette system as claimed in claim 1 comprising:

the second cover comprising a second child lock; and the second child lock engaging the second cover with the lateral cassette wall.

6. The medication blister cassette system as claimed in claim 1 comprising:

the cassette case comprising a second cover sensor;

the second cover sensor being positioned adjacent to the second cover; and the second cover sensor being electronically connected to the cassette microcomputer.

7. The medication blister cassette system as claimed in claim 1 comprising:

the cassette case comprising a blister housing sensor;

the blister housing sensor being positioned adjacent to the blister housing;

the blister housing sensor detecting the presence of the blister housing within the cassette case; and the blister housing sensor being electronically connected to the cassette microcomputer.

8. The medication blister cassette system as claimed in claim 1 comprising:

the cassette microcomputer comprising a medication package reader;

the medication package comprising a medication package identifier; and the medication package identifier being positioned adjacent to the medication package reader.

9. The medication blister cassette system as claimed in claim 1 comprising:

the cassette case comprising a medication package sensor;

the medication package sensor being positioned adjacent to the medication package;

the medication package sensor detecting the presence of the medication package within the cassette case; and the medication package sensor being electronically connected to the cassette microcomputer.

10. The medication blister cassette system as claimed in claim 1 comprising:

the blister housing comprising a plurality of compartment lights;

a corresponding compartment light among the plurality of compartment lights being accommodated within a corresponding blister housing compartment among the plurality of blister housing compartments; and the plurality of compartment lights being electronically connected to the cassette microcomputer.

* * * * *